United States Patent [19]
Wotiz et al.

[11] Patent Number: 5,312,752
[45] Date of Patent: May 17, 1994

[54] SPECIFIC ANTIBODIES AGAINST THE DNA-BINDING DOMAIN OF AND IMMUNOASSAYS TO DETERMINE THE PRESENCE AND FUNCTIONAL STATUS OF ESTROGEN RECEPTOR PROTEINS

[75] Inventors: Herbert H. Wotiz, Milton; Abdulmaged M. Traish, Belmont, both of Mass.

[73] Assignee: Trustees of Boston University, Boston, Mass.

[21] Appl. No.: 784,626

[22] Filed: Nov. 1, 1991

Related U.S. Application Data

[63] Continuation of Ser. No. 388,091, Jul. 31, 1989, abandoned.

[51] Int. Cl.⁵ .......................... C07K 15/28; C12N 5/12
[52] U.S. Cl. ........................... 435/240.27; 530/388.22; 530/387.1; 530/387.9; 530/388.1; 435/240.26
[58] Field of Search ............... 530/387.1, 387.9, 388.1, 530/388.22; 435/240.2, 240.26, 240.27

[56] References Cited

U.S. PATENT DOCUMENTS 4,215,102 7/1987 Lee .
4,232,001 11/1980 Jensen et al. .
4,293,536 10/1981 Jensen et al. .
4,711,856 12/1987 Spelsberg .

FOREIGN PATENT DOCUMENTS 0129669 1/1985 European Pat. Off. .

OTHER PUBLICATIONS

Green et al. (1986) Nature 320, 134–139.
Smith et al. (1988) Endocrinology 122, 2816–2825.
Kearney (1984) in "Fundamental Immunology" (W. E. Paul, Ed) Raven Press, New York, 751–766.
Traish et al., Steroids 55: 196–208 (1990).
Muller et al., J. Biol. Chem. 258: 9227–9236 (1983).
Notides, A. C., Receptor and Hormone Action, vol. II, Chap. 2, pp. 33–61, 1978.
Jensen et al., Advanced Experimental Medicine and Biology, vol. 36, pp. 60–79, 1973.
Robertson et al., Acta Endocrinol. 68: 534–542 (1971).
Cancer Research, vol. 46, No. 8, Supplement, Aug. 1986, pp. 4232s–4313s inclusive.
Muller et al., Endocrinology 116:337–345 (1985).
Muller et al., J. Biol. Chem. 258:11582–11589 (1983).
Muller, R. E. and A. M. Traish, Endocrinology of the Breast: Basic and Clinical Aspects, vol. 464, Ann. N.Y. Acad. Sci., pp. 200–217.
Parmar et al., J. Steroid Biochem. 31:359–364 (1988).
Traish et al., J. Biol Chem. 255:4068–4072 (1980).
Muller et al., J. Biol. Chem. 257:1295–1300 (1982).
Kumar et al., Cell 51:941–951 (1987).
Hill et al., Cancer Research 49:145–148 (1989).
Green et al., Nature 320:134–139 (1986).
Greene et al., Science 231:1150–1153 (1986).
Raam et al., Mol. Immunol. 18:143–156 (1981).
Greene et al., J. Steroid Biochem. 11:333–341 (1979).
Greene et al., Proc. Natl. Acad. Sci USA 74:3681–3685 (1977).

(List continued on next page.)

Primary Examiner—Robert A. Wax
Assistant Examiner—R. Keith Baker
Attorney, Agent, or Firm—David Prashker

[57] ABSTRACT

The present invention provides unique prepared immunogens, site-specific polyclonal antisera and monoclonal antibodies against the DNA-binding domain of estrogen receptor protein, and immunoassay to determine the functional status of estrogen receptors in a cellular sample. Collectively or individually the component parts of the invention provide the ability not only to identify accurately the presence of human estrogen receptor but also the capability of determining whether the estrogen receptor exists in a functional or non-functional state.

2 Claims, 25 Drawing Sheets

OTHER PUBLICATIONS

Greene et al., *Proc. Natl. Acad. Sci. USA* 77:157-161 (1980).
Faugue et al., *J. Biol. Chem.* 260:15547-15553 (1985).
Moncharmont et al., *Biochemistry* 23:3907-3912 (1984).
Raam et al., *Clin. Chem.* 32:1496-1502 (1986).
Raam, S. and D. M. Vrabel, *Clin. Chem.* 32:2053-2057 (1988).
Raam, S., *Steroids* 47:337-340 (1986).
Raam, S., *Clin. Chem.* 33:1107-1108 (1987).
Mueller, R. G. *Clin. Chem.* 33:1108-1109 (1987).
Borgna et al (1984) Biochemistry 23, 2162-2168.
Green et al (1984) J. Steroid. Biochem. 20, 51-56.
Smith et al (1988) Endocrinology 122, 2816-2825.
Walten et al (1983) in "Genetic Engineering: Principles and Methods," vol. 5 (Setlow & Hollaander, eds) Plenum Publishing Corp, 61-91.

```
      *       190                    *        200                *
Cys Ala Val Cys Asn Asp Tyr Ala Ser Gly Tyr His Tyr Gly Val Trp Ser Cys Glu Gly
  *                  210                              220 *
Cys Lys Ala Phe Phe Lys Arg Ser Ile Gln Gly His Asn Asp Tyr Met Cys Pro Ala Thr
          *          230                      *       240
Asn Gln Cys Thr Ile Asp Lys Asn Arg Arg Lys Ser Cys Gln Ala Cys Arg Leu Arg Lys
                     250                            PEPTIDE 2       260
Cys Tyr Glu Val Gly Met Met Lys Gly Gly Ile Arg Lys Asp Arg Arg Gly
                                        PEPTIDE 3
```

FIG. I

○ CONTROL WITH PREIMMUNE SERUM
● 10-FOLD DILUTION
△ 50-FOLD DILUTION
▲ 100-FOLD DILUTION
FRACTION 40 REPRESENTS THE TOP OF THE GRADIENT

○ CONTROL WITH PREIMMUNE SERUM

● 10-FOLD DILUTION

△ 50-FOLD DILUTION

▲ 100-FOLD DILUTION

FRACTION 40 REPRESENTS THE TOP OF THE GRADIENT o CONTROL (ER ONLY)
● AT2A
△ AT3A
▲ AT3B
FRACTION 40 REPRSENTS THE TOP OF THE GRADIENT o CONTROL (ER ONLY)
o AT2A
△ AT3A
▲ AT3B
FRACTION 40 REPRESENTS THE TOP OF THE GRADIENT

○ CONTROL WITH ANTISERUM, EXCEPT FOR ER WHICH WAS INCUBATED WITH PREIMMUNE SERUM.

● ADDITION OF ANTISERUM AT3A

△ ANTISERUM AT3B

FRACTION 40 REPRESENTS THE TOP OF THE GRADIENT

○ CONTROL WITHOUT PREIMMUNE SERUM

● ANTISERUM AT2A

△ ANTSERUM AT3A

▲ ANTISERUM AT3B

FRACTION 40 REPRESENTS THE TOP OF THE GRADIENT

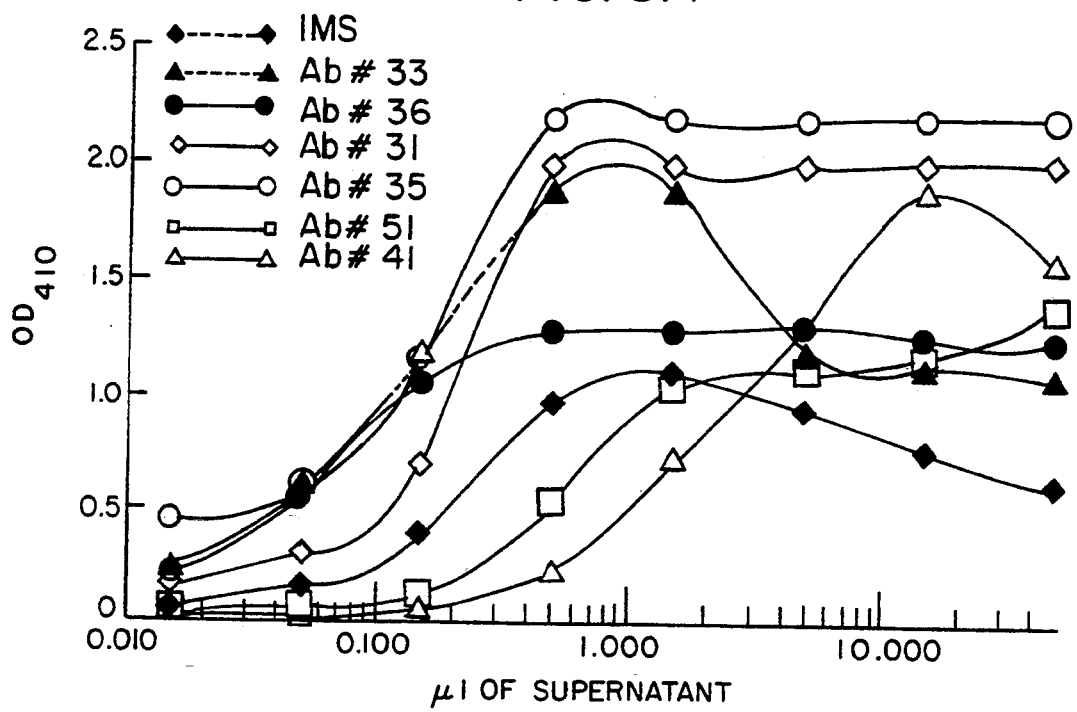
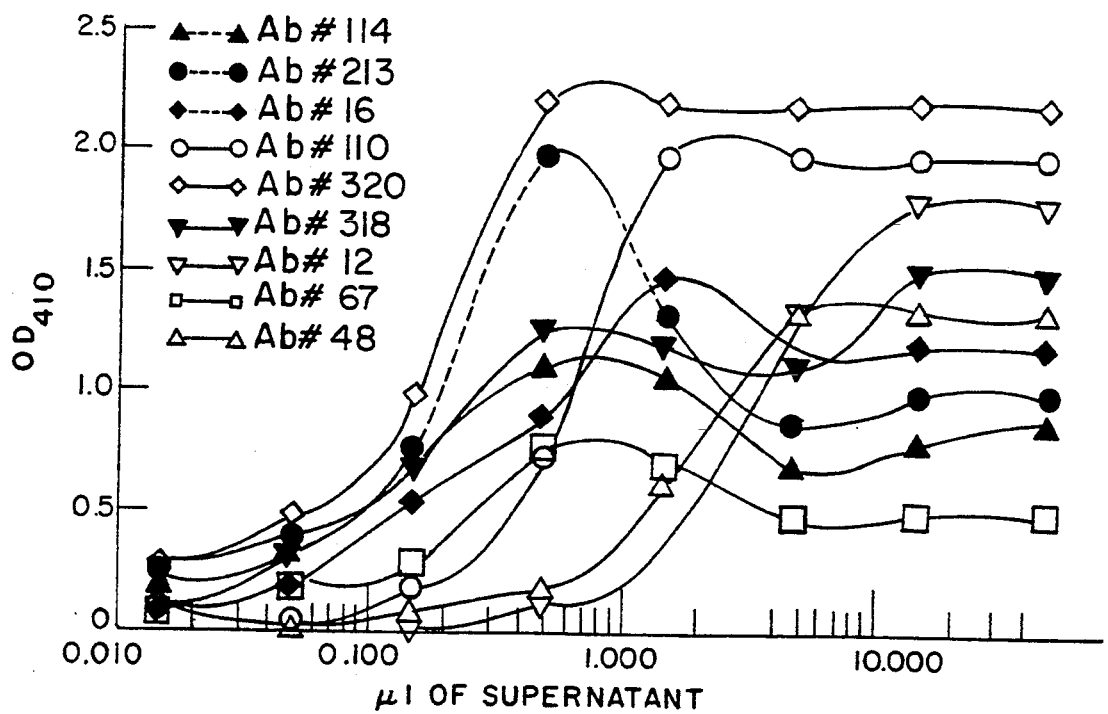

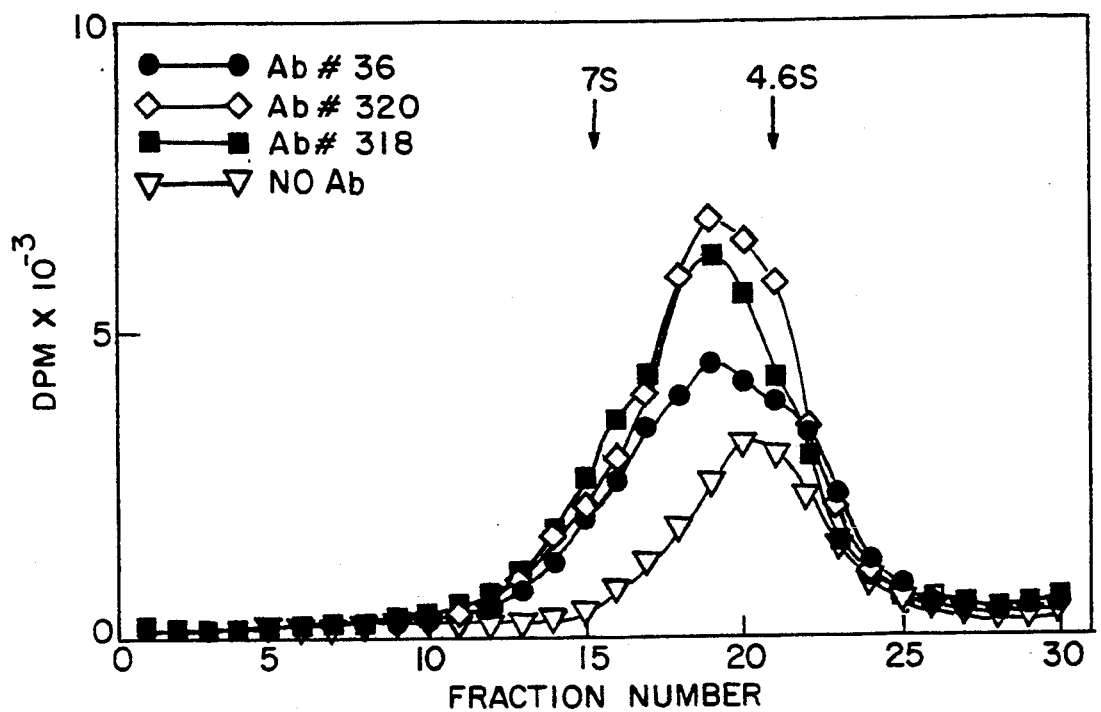
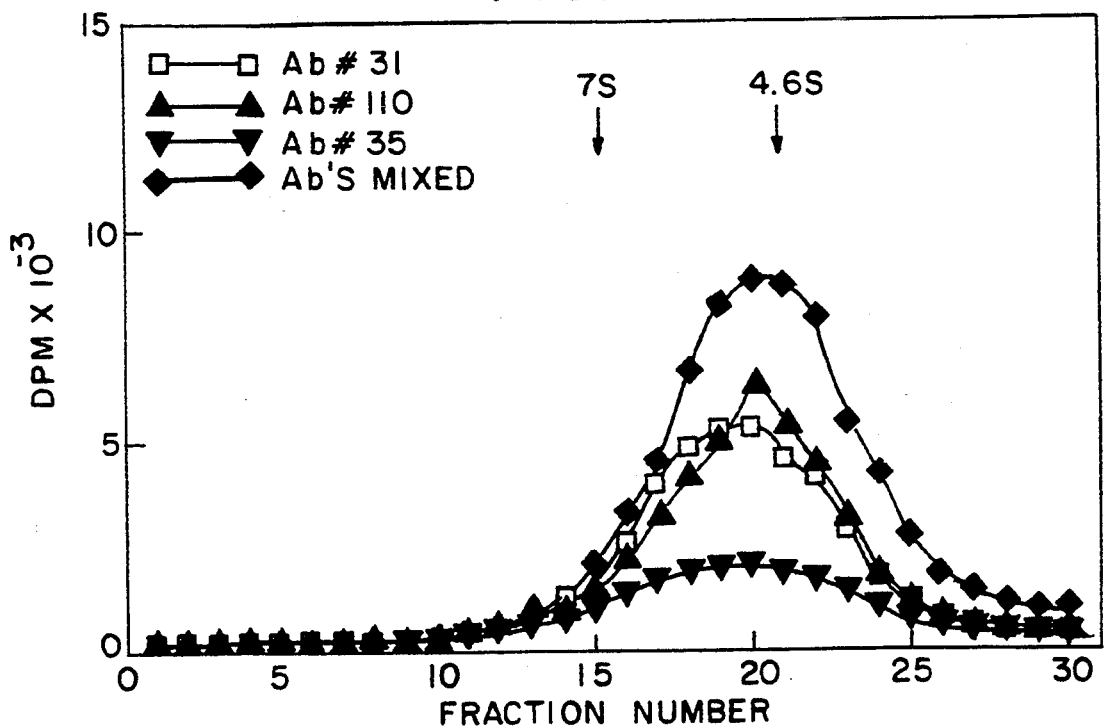

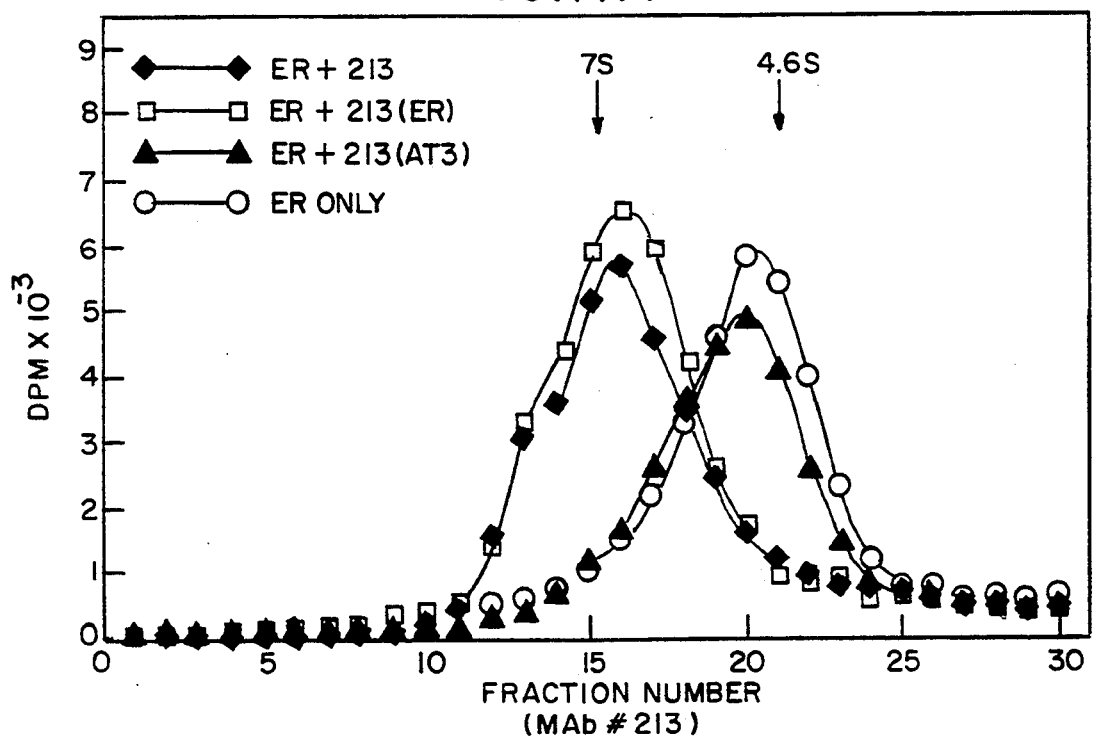
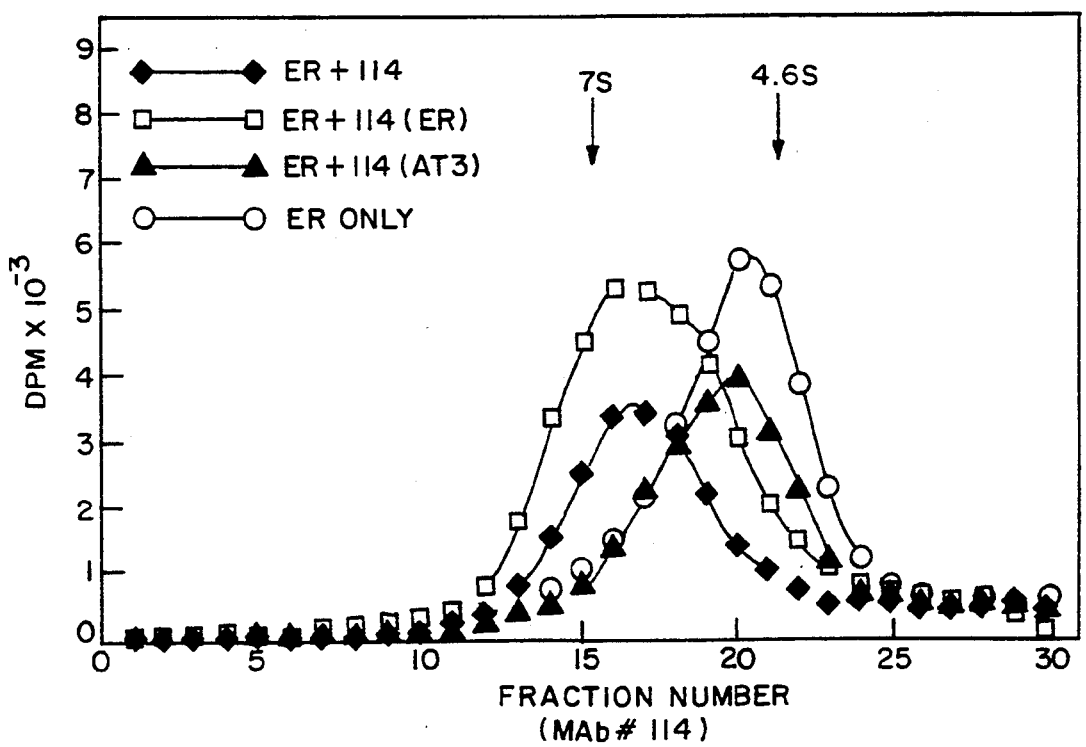

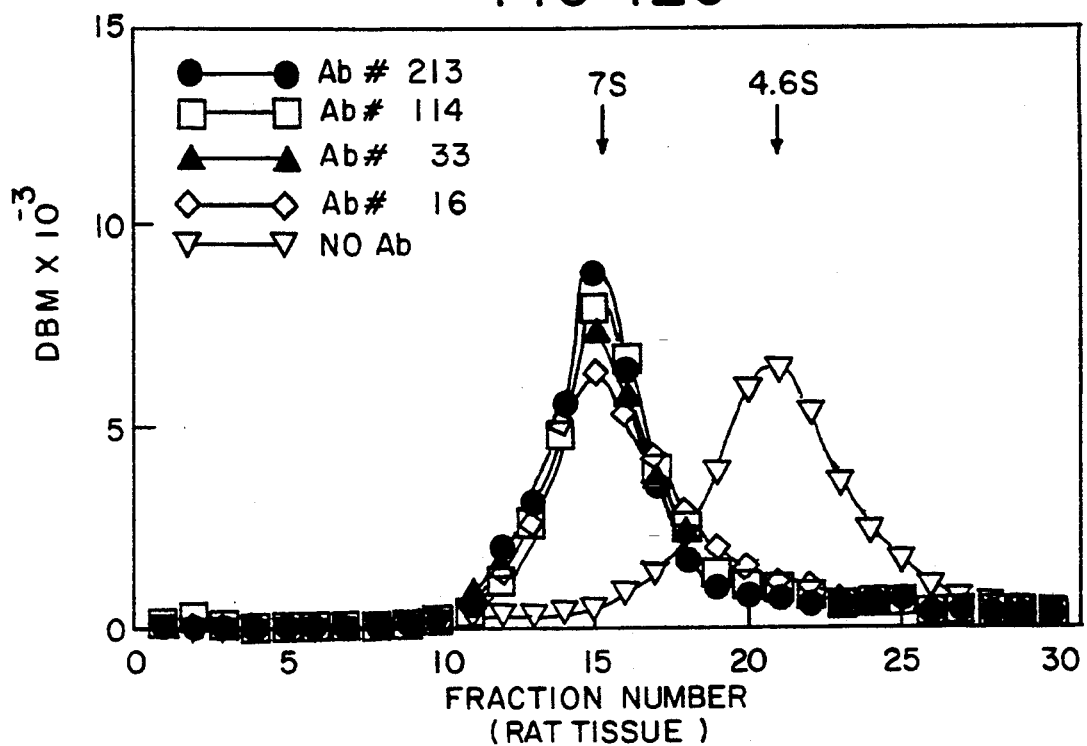
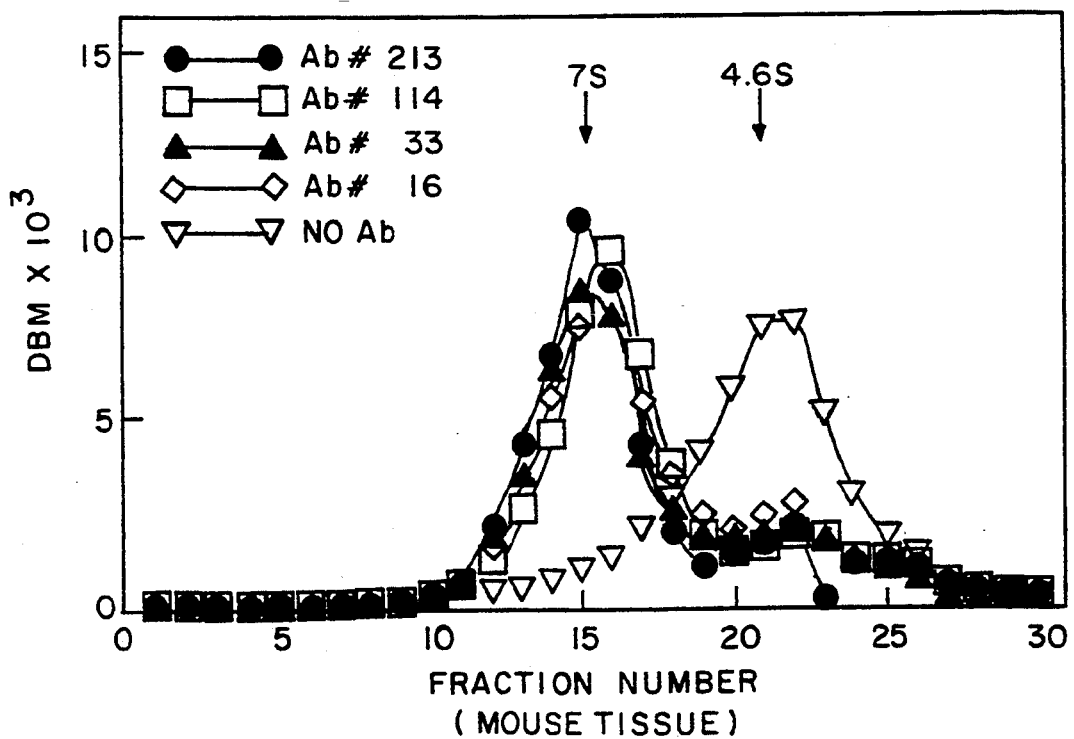

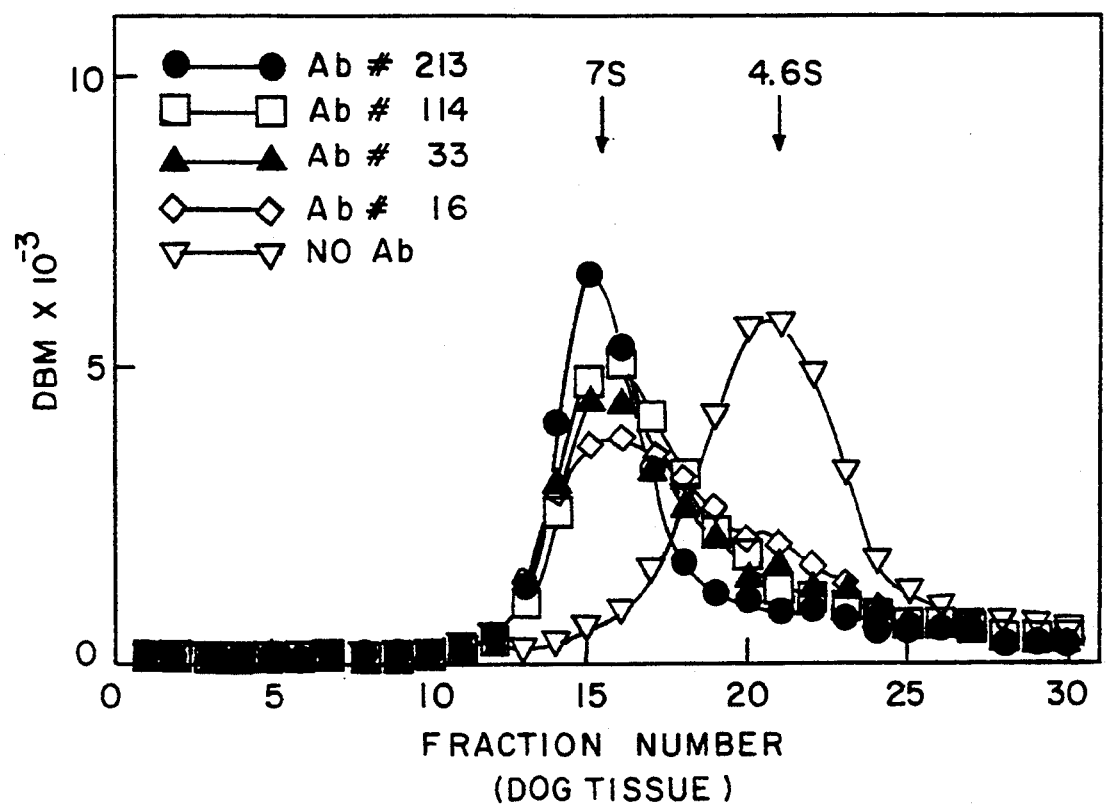

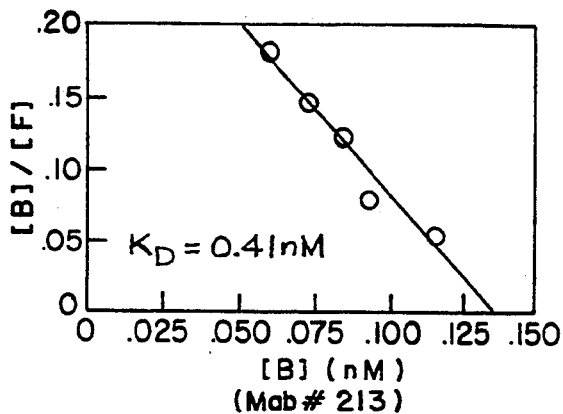
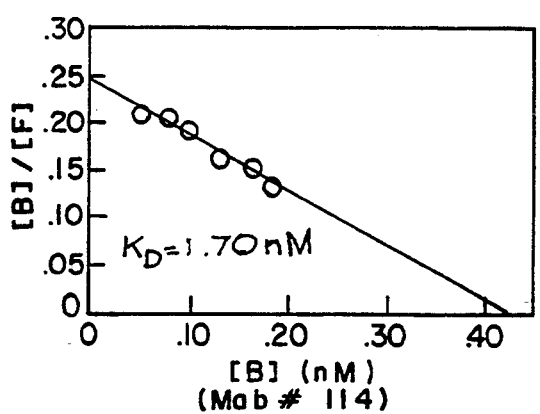
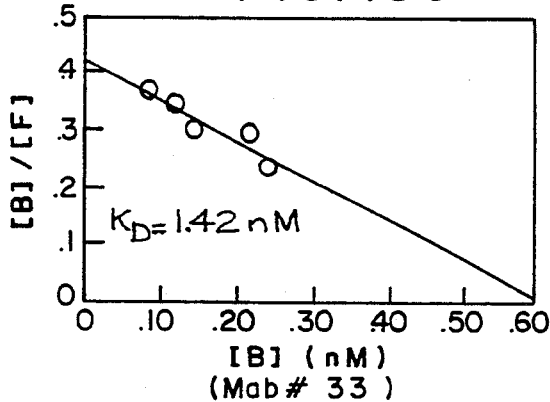
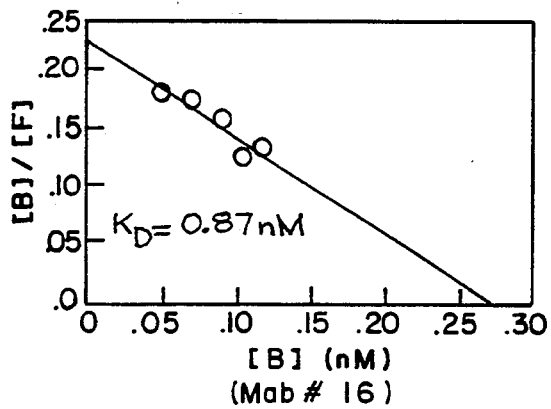
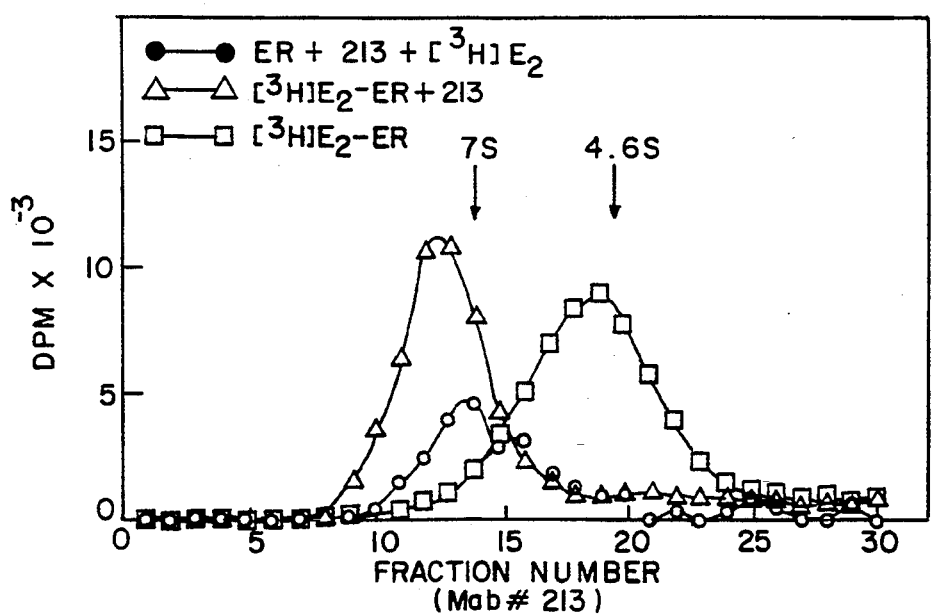

SPECIFIC ANTIBODIES AGAINST THE DNA-BINDING DOMAIN OF AND IMMUNOASSAYS TO DETERMINE THE PRESENCE AND FUNCTIONAL STATUS OF ESTROGEN RECEPTOR PROTEINS

This application is a continuation of application Ser. No. 388,091, filed Jul. 31, 1989, now abandoned.

FIELD OF THE INVENTION

The present invention is concerned with the development of site-specific monoclonal and polyclonal antibodies raised against preselected functional domains within estrogen receptor protein; and is particularly directed to the use of specific monoclonal and polyclonal antibodies directed against the DNA-binding domain of human estrogen receptor as a means for evaluating the functionality of estrogen receptors in vitro.

BACKGROUND OF THE INVENTION

Estrogens are a class of naturally occurring steroid hormones which are produced in the ovaries and other tissues in the body and which directly influence the growth and function of specific target tissues and organs in humans and animals. These specific tissues and organs include the mammary gland, uterus, pituitary, brain, and liver. Although a variety of naturally occurring and chemically synthesized estrogens have been identified and characterized, perhaps the best known is the endogenous estrogen estradiol-17β (also known as $E_2$).

Estrogens as a class of hormones mediate their action by binding to an intracellular protein identified as "estrogen receptor" (also termed "ER"). The presence of this intracellular ER both provides and accounts for both cell proliferation and protein synthesis by estrogen dependent cells. The estrogen receptor in the absence of the estrogen hormone is biologically inactive both in vivo and in vitro; and, if the cells or tissues are homogenized and fractionated into cytosol and nuclear fractions, the estrogen receptor is found as a soluble protein in the cytosol. Although the precise interactions remain poorly understood, the generally accepted mechanism of action and sequence of events is believed to be as follows: When an estrogen such as estradiol is introduced to the target cells and tissues, there is specific binding between the estrogen and the ER protein which results in the formation of an estrogen/receptor protein complex. Also, at a time subsequent to hormone binding, a process termed activation and/or transformation ensues which leads to the formation of functional estrogen/hormone receptor complexes having a high affinity for the nuclear components, the DNA, of the target cell. Once the hormone/receptor protein complex is physically formed, it is said to translocate as a complex into the nucleus of the cell where it binds to the chromatin at specific binding sites on the chromosomes and initiates messenger ribonucleic acid (mRNA) transcription. New messenger RNA is then synthesized, chemically modified, and exported from the nucleus into the cytoplasm of the cell where ribosomes translate the mRNA into new proteins. This is the well recognized estrogenic effect on the cell—that is, the initiation of new protein synthesis and concomitant new cell growth/proliferation. The theoretical premise and the generally accepted, though poorly understood, mechanism of action regarding estrogen and estrogen receptor proteins and their interactions are described in greater detail by the following publications which are merely representative of the ongoing investigations in this field. These are: Mester et al., *Exp. Cell. Res.* 81:447-452 (1973); King and Greene, *Nature* 307:745-747 (1984); Welshons et al., *Nature* 307:747-749 (1984); Gorski and Gannon, *Annu. Rev. Physiol.* 38:425-450 (1976); Gorski et al., *Recent Prog. Horm. Res.* 24:45-72 (1968); Jordan, V., *Pharmacological Reviews* 36:245-276 (1984).

In order to truly appreciate the background of the present invention, it is useful to summarize in depth the major details and sequential events believed to be in effect regarding the intracellular protein referred to as "estrogen receptor". In the unbound state, and in the absence of an estrogen, the estrogen receptor protein can be located in vitro within the cytosol and is a single protein composed of 595 amino acids. The molecular weight of ER determined from gel electrophoresis and other physical methods is approximately 67,000 daltons. In soluble systems and under set conditions, the ER protein can be found in various molecular forms which sediment at either 8S, 5S, or 4S values as determined by sucrose density gradient analysis. The 8S form of ER is believed to be the unactivated, untransformed form of the ER protein associated with the unbound, inactive state of estrogen receptor in the absence of estrogens. The 8S ER form is a large molecular weight complex, presumably associated with heat shock proteins, that does not bind efficiently to nuclei or DNA in vitro and is stabilized as a macromolecule by sodium molybdate.

In comparison, the 4S ER protein form is a monomeric protein molecule that can be generated from the 8S form in vitro by treatment with high ionic strength buffers or by increasing salt concentrations (KCl or NaCl). The 4S ER form binds to both nuclei and DNA-cellulose in vitro; it is generally termed the "activated but untransformed" estrogen receptor protein. From the published reports, it appears that the dissociation of the 8S ER form into the 4S form initiates either a major change in the sterochemical conformation of the protein or a direct exposure of the previously hidden DNA binding domain of the molecule.

Alternatively, the 5S form of ER is a dimeric protein molecule which is created by the conversion of the 4S ER protein via a bimolecular reaction which is facilitated by elevated temperatures and/or dilution after KCl activation. The 5S form of ER can be generated in vitro by incubation of either the 8S or 4S forms at 28°-30° C. for 30-45 minutes in the absence of transformation inhibitors. It is generally believed that the 5S form of ER is both "activated and transformed" and therefore is the biologically active entity which binds to the DNA within the nuclei. Moreover, it is also this 5S form which is found associated with the nuclei subsequent to the administration of estradiol in vivo.

It will be appreciated that the present state of knowledge regarding the various forms of estrogen receptor protein have been obtained and characterized via many different investigations employing physical and chemical forms of analysis. Merely representative of these various investigations and reports are the following: Muller et al., *Endocrinology* 116:337-345 (1985); Muller et al., *J. Biol. Chem.* 258:11582-11589 (1983); *Endocrinology Of The Breast: Basic And Clinical Aspects*, Volume 464, Annals Of The New York Academy Of Sciences, pages 202-217, 1986; Parmar et al., *J. Steroid Biochem.* 31:359-364 (1988); Traish et al., *J. Biol. Chem.*

255:4068–4072 (1980); and Muller et al., *J. Biol. Chem.* 257:1295–1300 (1982).

It is essential also to recognize that estrogen receptor protein, particularly from human sources, has been investigated and evaluated in terms of functional domains which provide and are responsible for the characteristic biological and physiological properties individually. The complementary DNA (cDNA) of human estrogen receptor has been cloned which, in turn, has lead directly to the elucidation of the human ER protein primary sequence. Subsequent studies have further defined the various functional domains of human ER protein as comparing six different regions, each of which functionally provides different properties and characteristics. Each of the six functional domains have been designated as a region "A-E" respectively. Regions A and B span the first 180 amino acids within ER proteins and have yet to be assigned a precise function in gene expression, although it is postulated that they are required for full functional activity in certain types of cells or for interaction with specific kinds of genes. Region C, which encompasses the amino acid segment 185–263 of human ER protein, is a critical region for biological activity because it is this amino acid segment which is necessary for binding of the ER protein to genomic DNA to occur. This functional domain and its DNA-binding ability is essential for eliciting the estrogen mediated biological response in vivo. Region D is believed to be the hinge area of the protein with as yet an undefined function. Region E is believed to be the steroid binding domain because this region comprises an amino acid sequence which is generally shared between different classes of receptors for steroids. Region F has yet to be assigned a specific function. It is important to note that regions C and E are said to be conserved among all the steroid receptor family members throughout the different classes—thereby indicating that these specific regions are critical for hormone receptor function generally within steroids as a family. Specific publications describing these investigations, data, and conclusions in greater detail are represented by the following: Kumar et al., *Cell* 51:941–951 (1987); Hill et al., *Cancer Res.* 49:145–148 (1989); Greene et al., *Nature* 320:134–139 (1986); and Greene et al., *Science* 231:1150–1153 (1986).

Overall, it will be noted and appreciated that many investigations of ER protein and the characterization of hormone/ER complexes involve immunological methods and assays. A variety of different polyclonal antisera have been prepared against estrogen receptor protein; and against the nuclear binding estradiol-receptor complex typically identified as "estrophilin" [Raam et al., *Mol. Immunol.* 18:143–156 (1981); Greene et al., *J. Ster. Biochem.* 11:333–341 (1979); Greene et al., *Proc. Natl. Acad. Sci. USA* 74:3681–3685 (1977)]. Similarly, a large variety of monoclonal antibodies against human and animal estrogen receptor proteins and estrophilins have been prepared for many different investigational purposes [Greene et al., *Proc. Natl. Acad. Sci. USA* 74:3681 (1977); Greene et al., *Proc. Natl. Acad. Sci. USA* 77:157–161 (1980); Greene et al., *Proc. Natl. Acad. Sci. USA* 77:5515 (1980); Borgna et al., *Biochem.* 23:2162–2168 (1984); Fauque et al., *J. Biol. Chem.* 260:15547–15553 (1985); and Moncharmont et al., *Biochemistry* 23:3907–3912 (1984)].

The common flaw and recurring problem of these known polyclonal and monoclonal antibodies is their uniform and consistent failure to be site specific. This failure, in turn, produces erroneous empirical results and unreliable information—not only for investigational purposes but also in clinical applications of such antibodies for therapeutic purposes. As a major example, the measurement of estrogen receptors in human breast carcinomas has been the primary tool and favored diagnostic method for choosing between hormonal and cytotoxic chemotherapy when treating breast cancer patients. A variety of different immunoassays employing anti-ER antibodies are presently known and used for this purpose. These are exemplified by the following publications: U.S. Pat. Nos. 4,232,001; 4,293,536; 4,215,102; and 4,711,856. See also European Patent Application Publication No. A2-0129669 published Jan. 2, 1985. Unfortunately, the immunoassays employing conventionally obtained monoclonal antibodies for these measurements have been found to be frequently unreliable and often non-specific. The nature and variety of problems of these unreliable and non-specific monoclonal antibodies are illustrated by the following publications: Raam, S. and D.M. Vrabel, *Clin. Chem.* 32:1496–1502 (1986); Raam, S. and D.M. Vrabel, *Clin. Chem.* 34:2053–2057 (1988); Raam, S., *Steroids* 47:337–340 (1986); and Raam, S., *Clin. Chem.* 33:1107–1108 (1987). Clearly, therefore, given all the presently known antibodies, assays, and immunological techniques, one still cannot accurately predict which of these estrogen receptor positive tumors will respond to hormonal treatment.

The causes of the present dilemma are in fact two fold: First is the failure of the monoclonal antibodies and polyclonal antisera to be sufficiently site-specific in order to demonstrate the presence of estrogen receptor in its various forms. Second is the failure (in so far as is presently known) to be able to identify functional status of this receptor protein using immunoassay systems. It is now clearly apparent to practitioners and clinicians ordinarily skilled in this art that so long as these insufficiently specific antibodies remain in clinical use, many repetitive failures in the known immunoassay systems will occur; and the ability to identify that proportion of breast cancer patients which would be sensitive and responsive to estrogen hormonal treatment will remain plagued with uncertainty and inaccuracy. For these reasons, the development of site-specific antibodies which could be employed within conventionally known diagnostic immunoassays would therefore be recognized generally as a major advance and fundamental improvement in antibody materials, assay reliability, and therapeutic benefit.

SUMMARY OF THE PRESENT INVENTION

The present invention is a multi-part innovation whose components may be employed individually but which should be employed collectively and cumulatively for maximum use and advantage. The individual component parts include unique prepared immunogens; site-specific monoclonal antibodies and polyclonal antisera; and improved immunoassays employing these site-specific antibodies. The prepared immunogen is able to cause the formation of domain specific antibodies against an estrogen receptor protein and comprises: an oligopeptide having an amino acid sequence comprised of at least a portion of the amino acids found within the DNA-binding, domain of an estrogen receptor protein; and a carrier protein bound to the oligopeptide.

The antibody components include polyclonal antisera specific for at least a portion of the DNA-binding domain of an estrogen receptor protein; and monoclonal antibodies specific for at least a portion of the DNA-binding domain of an estrogen receptor protein.

In addition, a variety of in vitro methods to identify the functional status of an estrogen receptor are provided using monoclonal antibodies and polyclonal antisera. These assays identify the presence of unactivated; and/or activated but untransformed; and both activated and transformed forms of estrogen receptor protein.

DETAILED DESCRIPTION OF THE FIGURES

The present invention may be more easily and completely understood when taken in conjunction with the accompanying drawing, in which:

FIG. 1 is a representation of the amino acid sequence of the DNA-binding, domain of human estrogen receptor from human breast cancer cells;

Figure 3A:
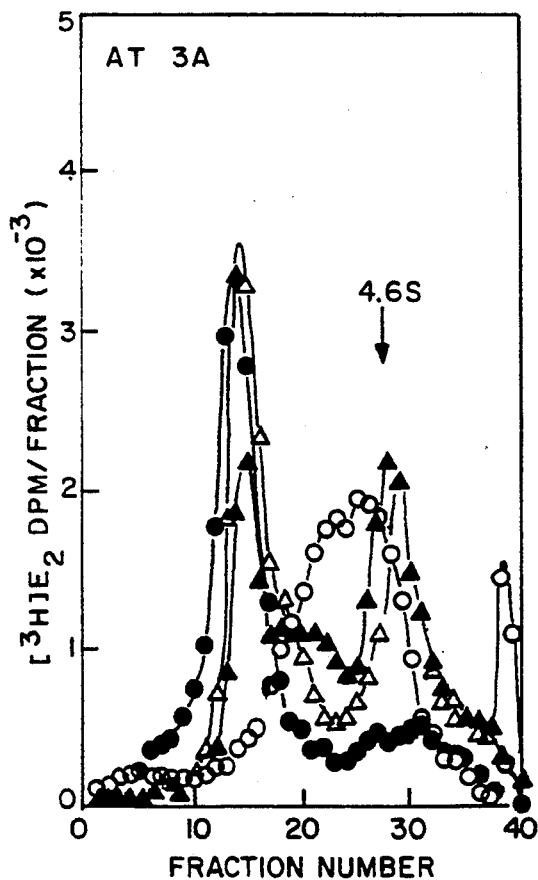
Figure 3B:
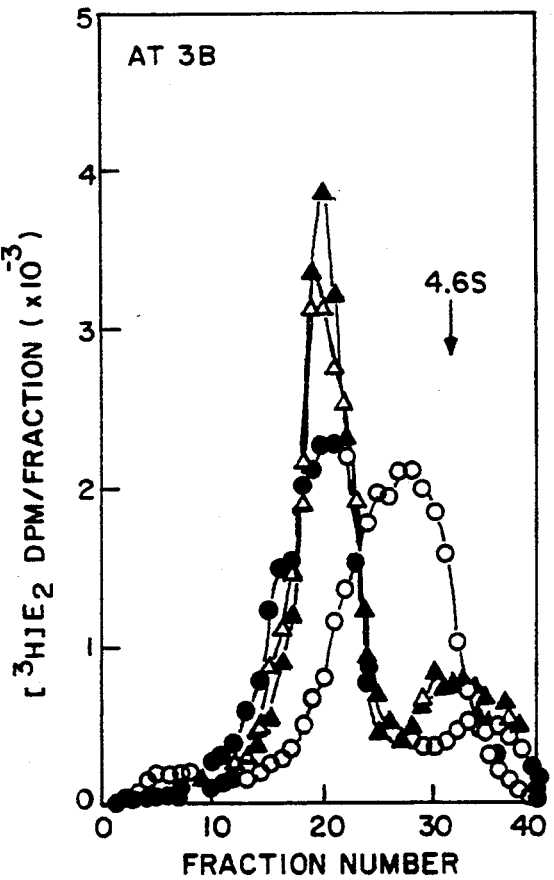
Figure 3C:
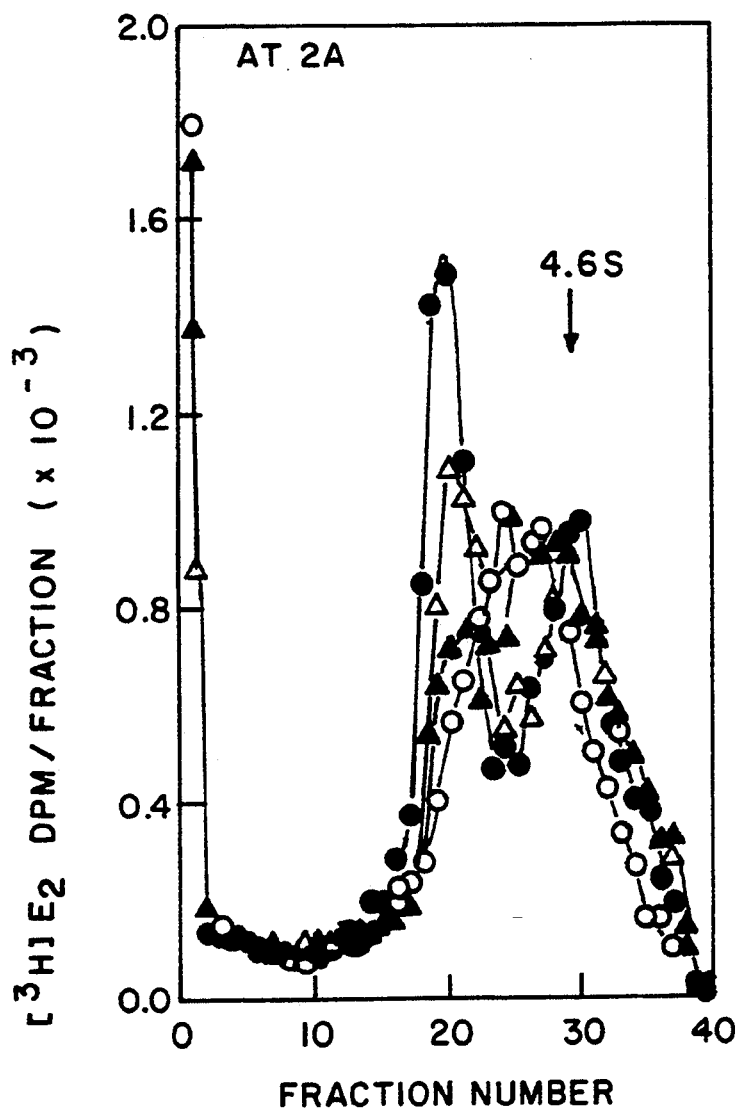
Figure 4A:
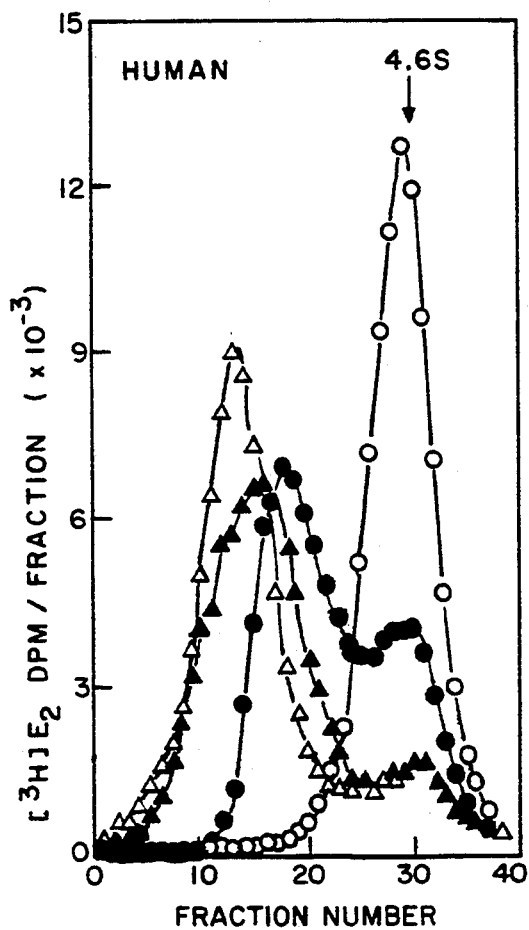
Figure 4B:
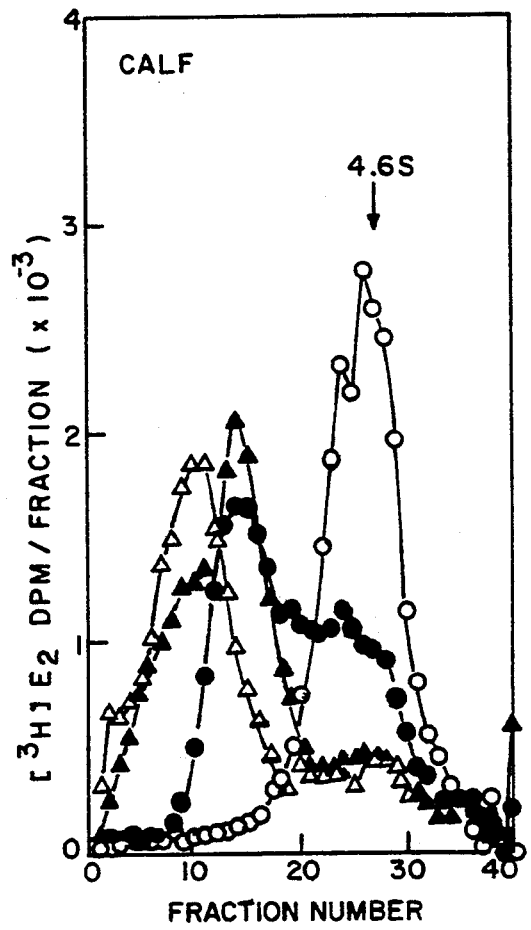
Figure 4C:
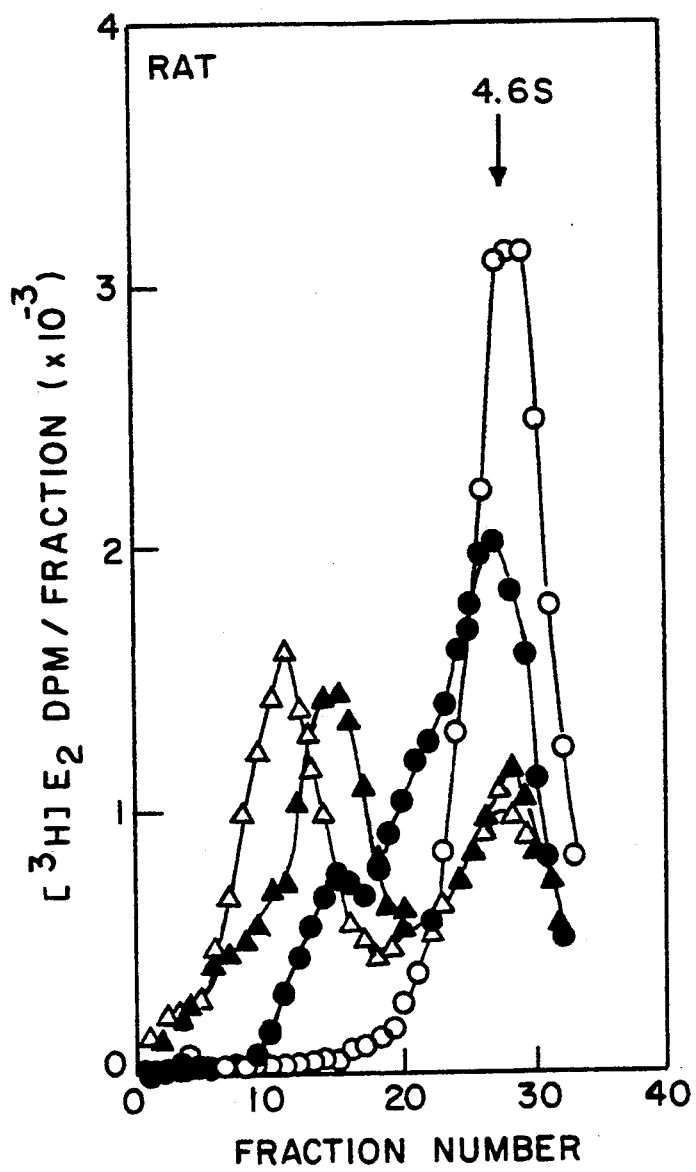
Figure 5D:
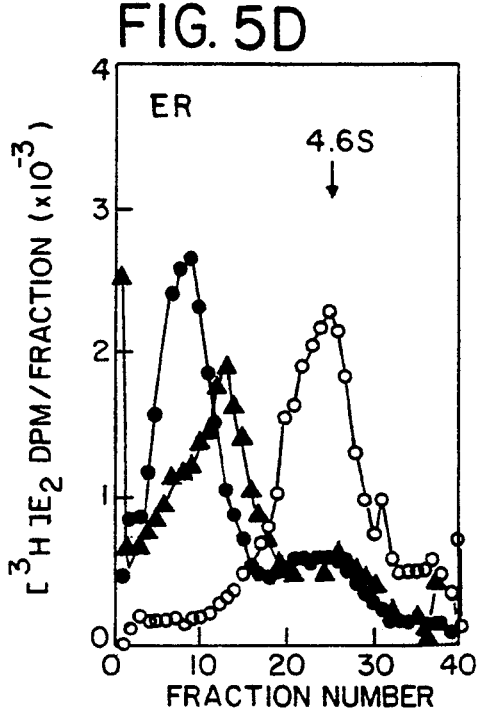
Figure 5A:
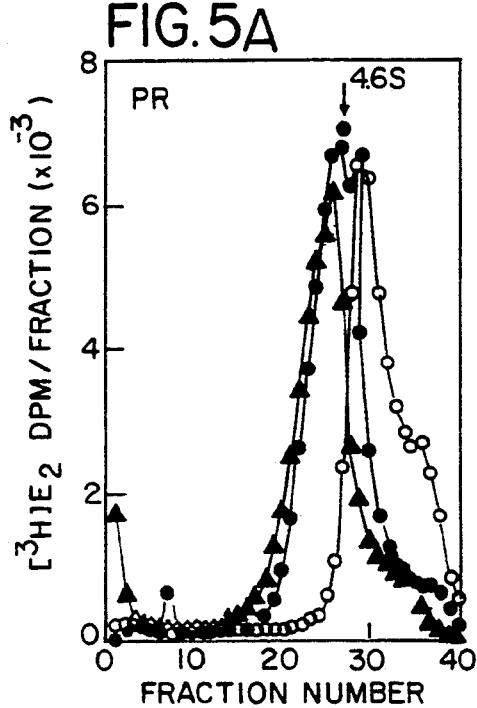
Figure 5C:
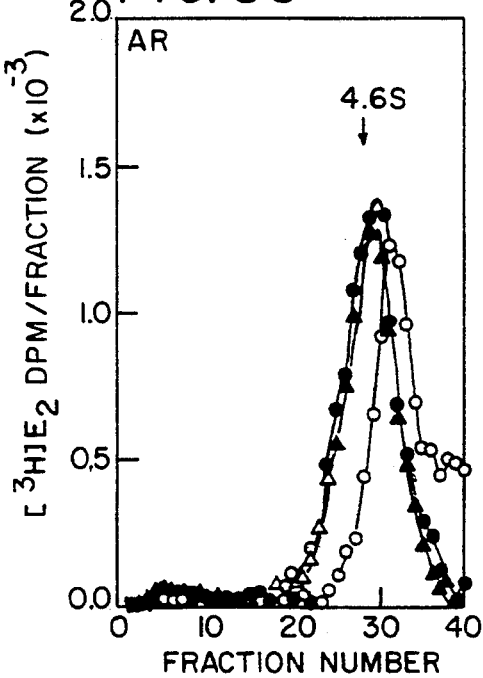
Figure 5B:
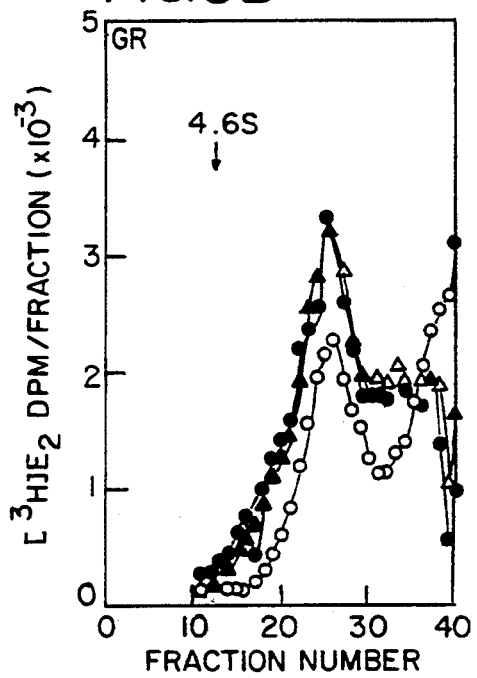
Figure 6:
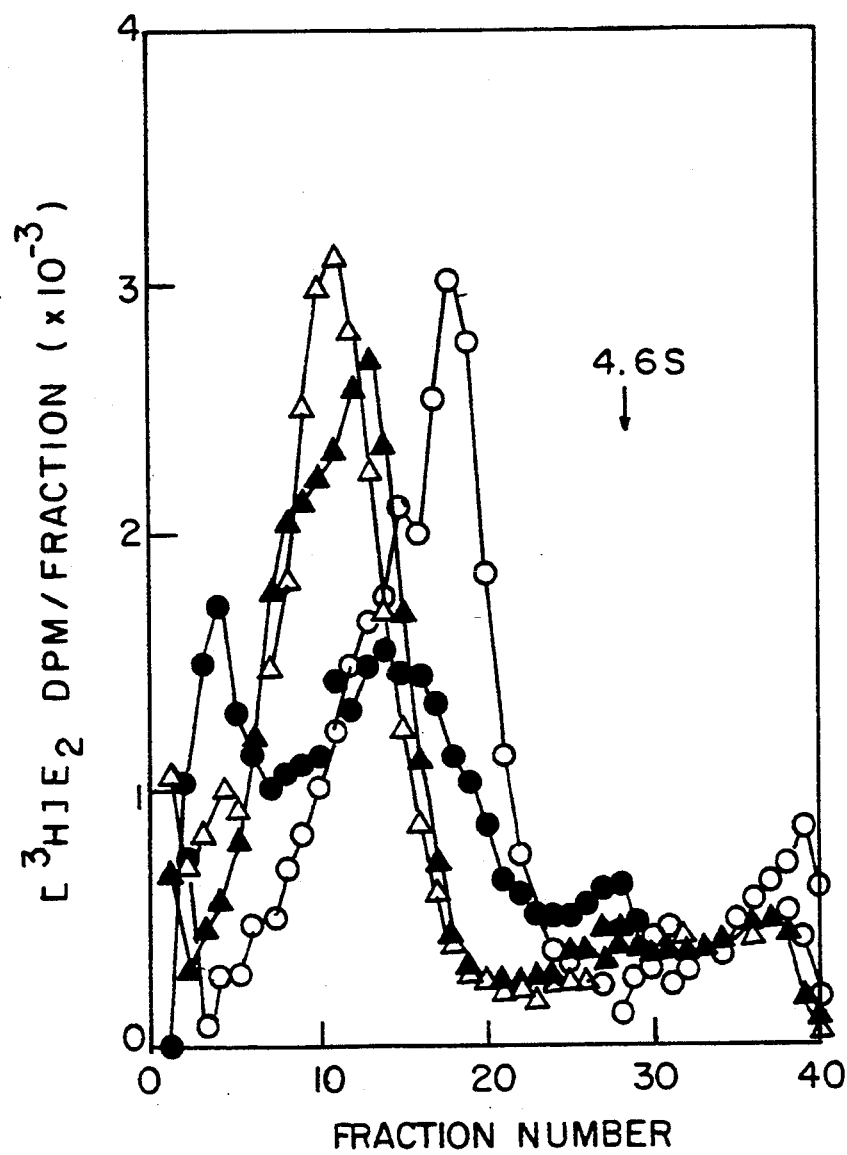
Figure 7:
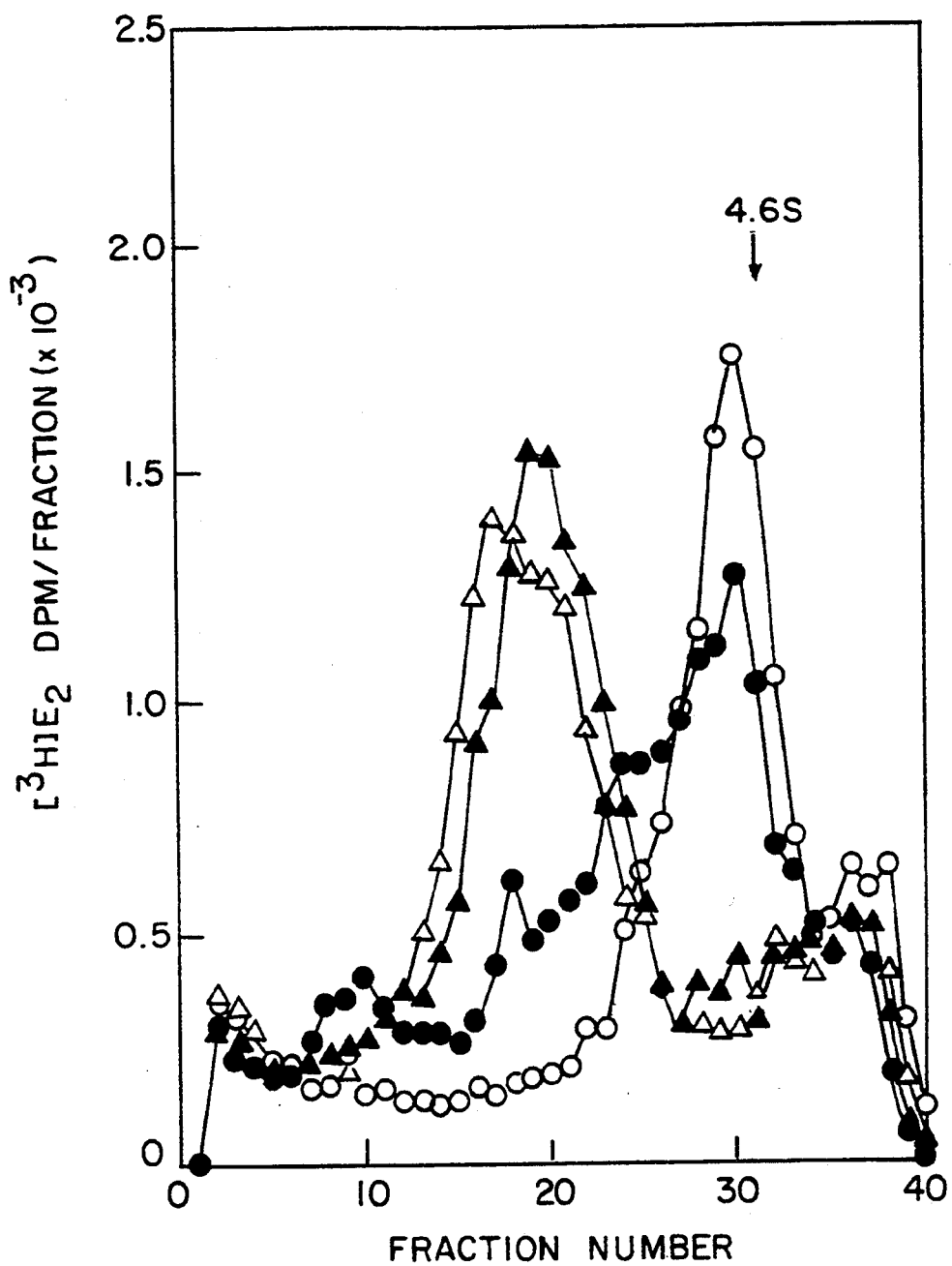
Figure 9:
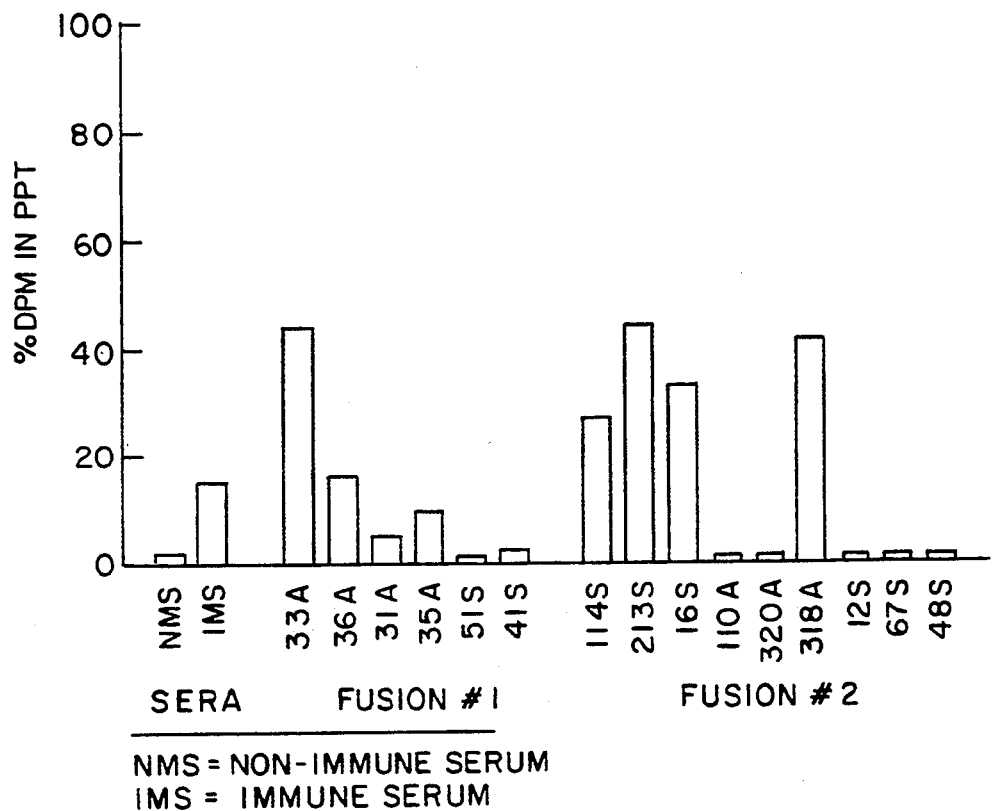
Figure 10A:
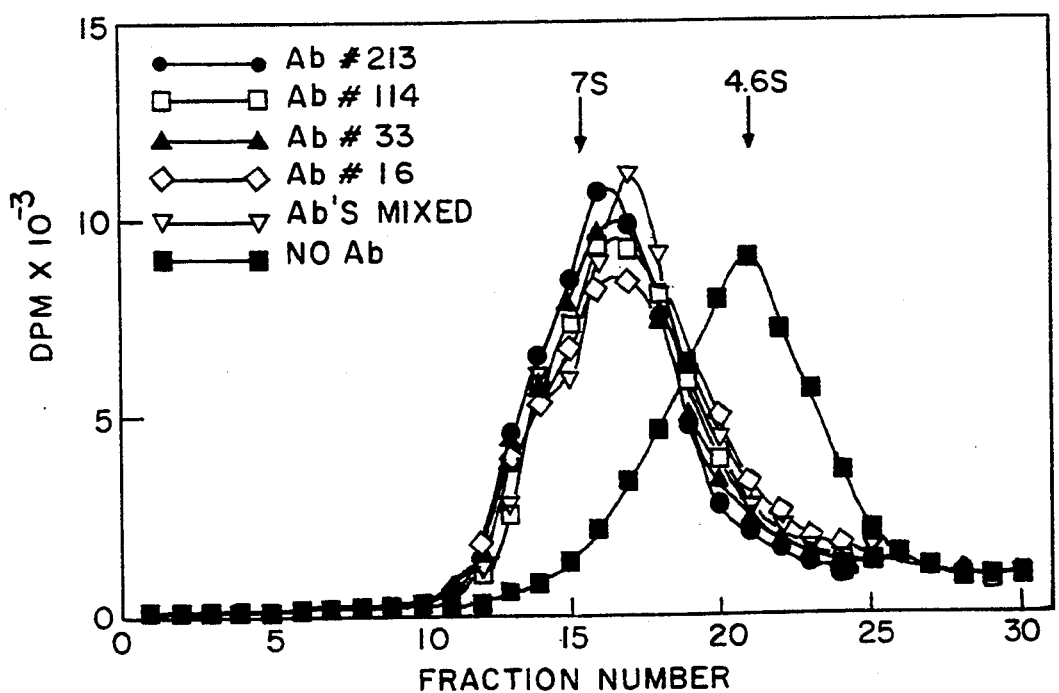
Figure 11B:
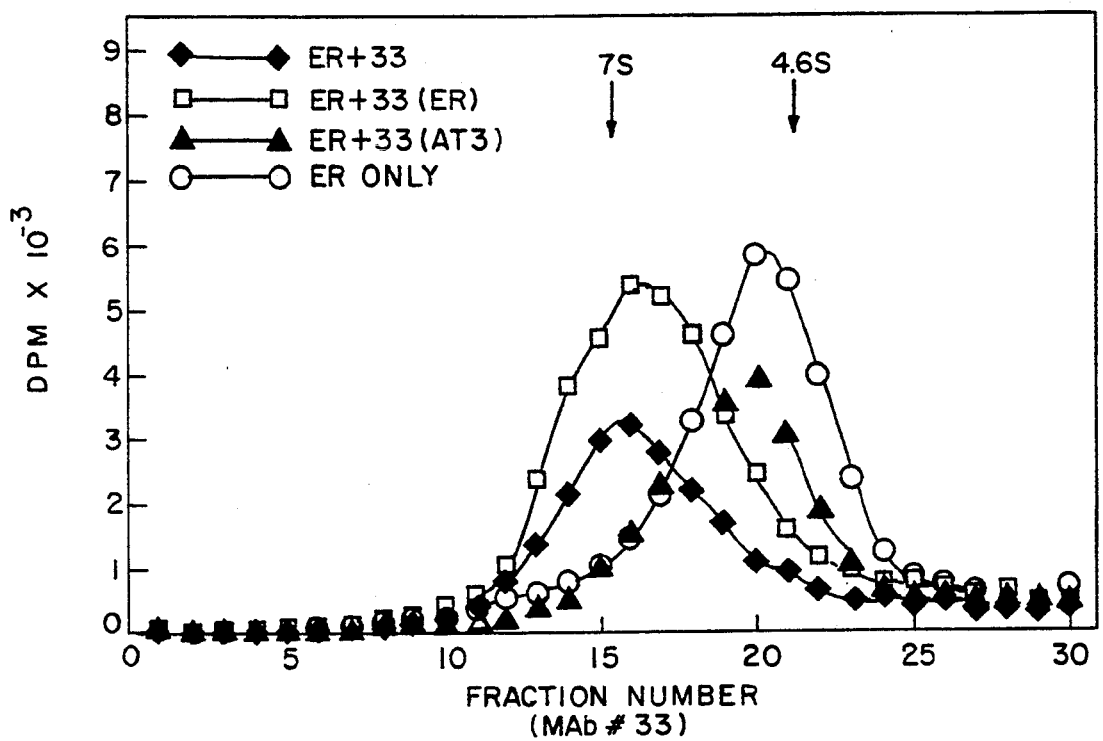
Figure 11D:
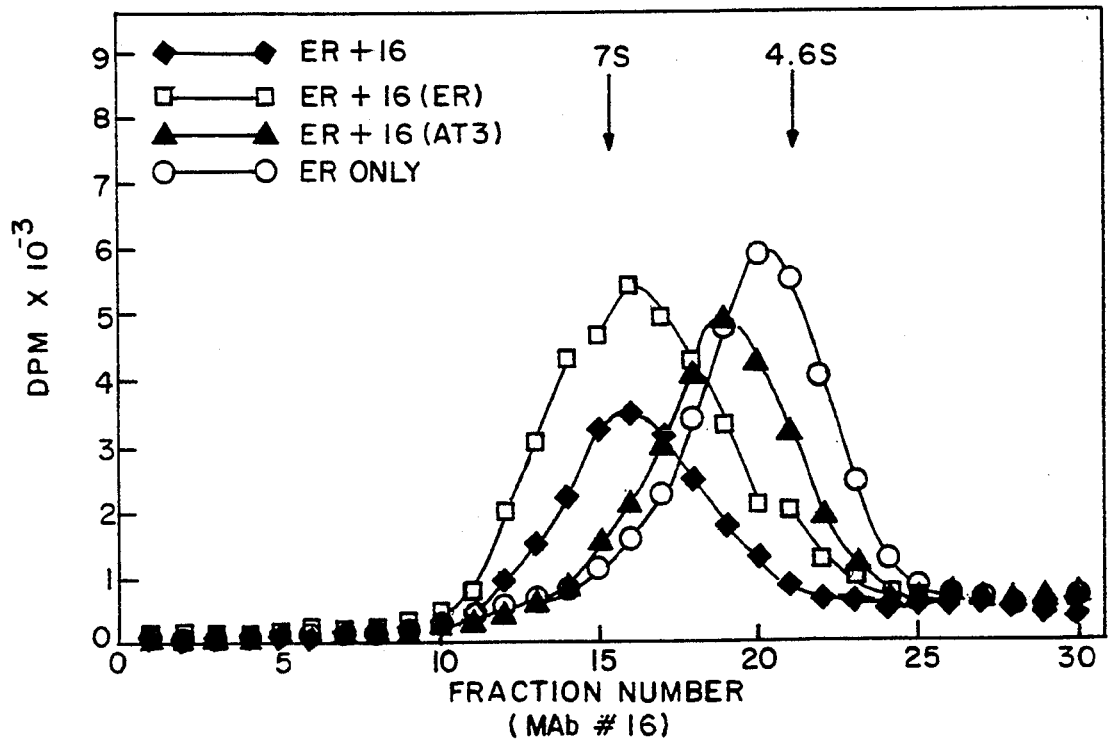
Figure 14A:
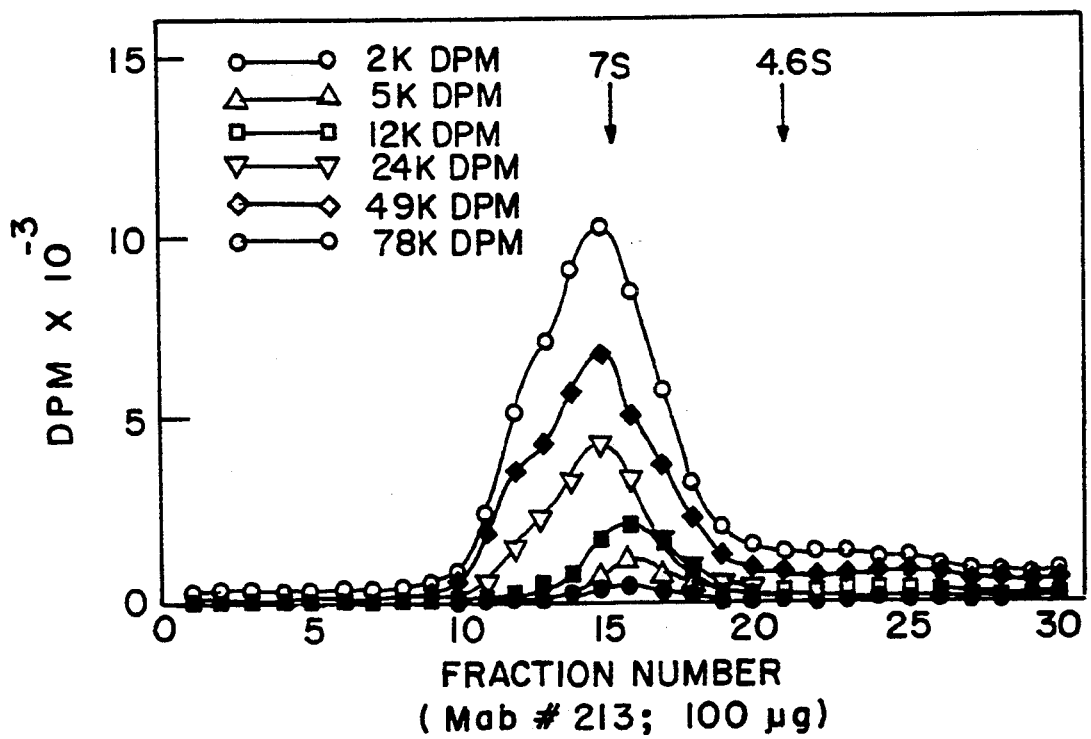
Figure 14B:
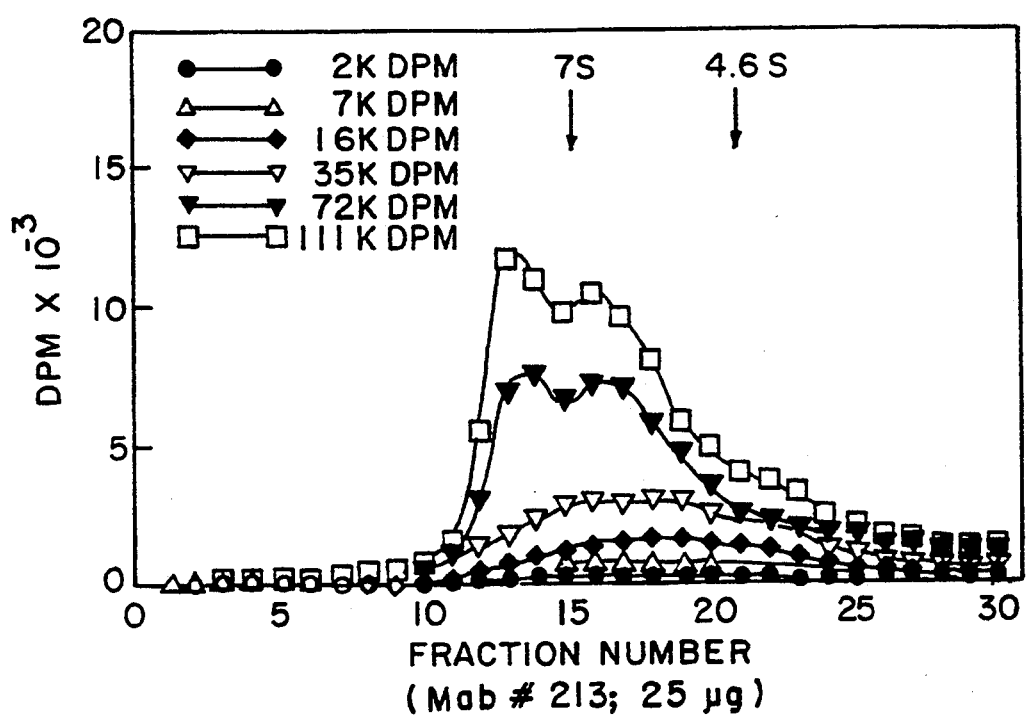
Figure 14C:
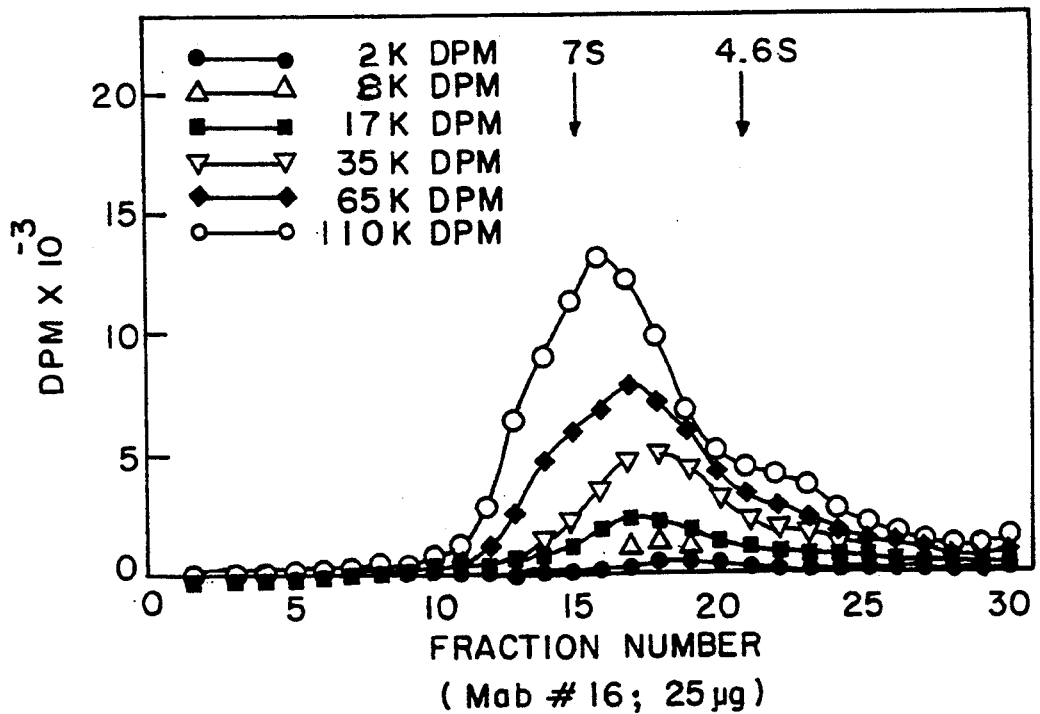
Figure 17:
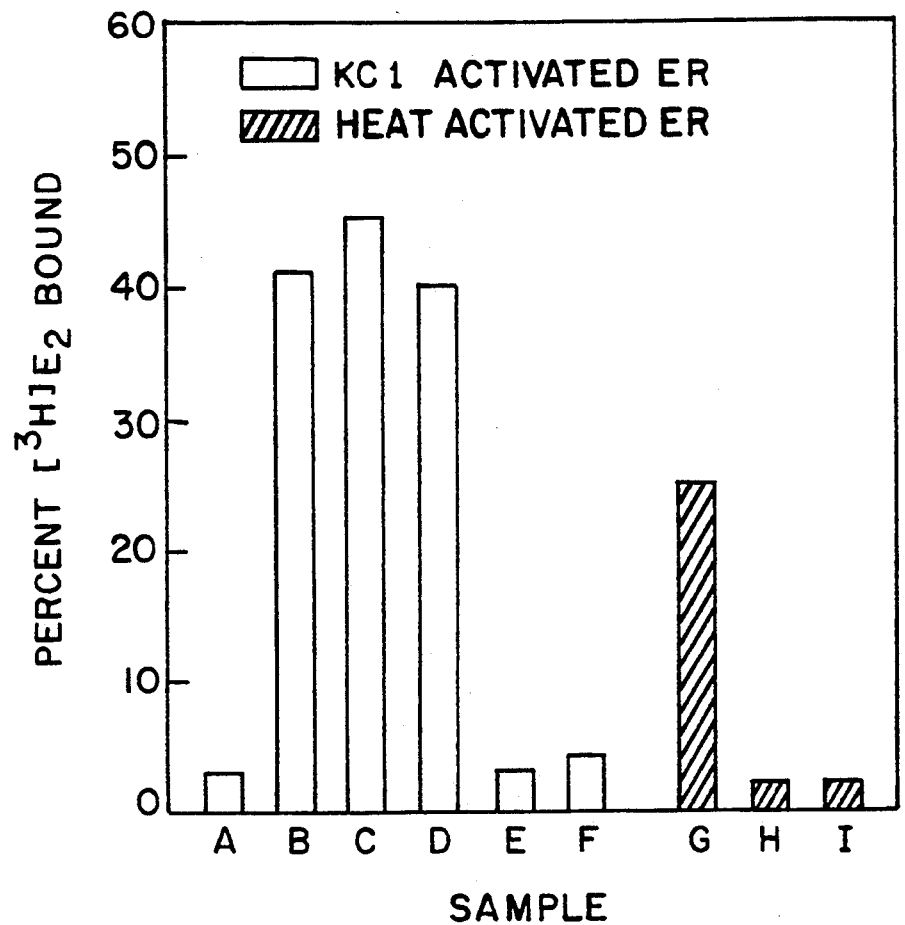
Figure 18:
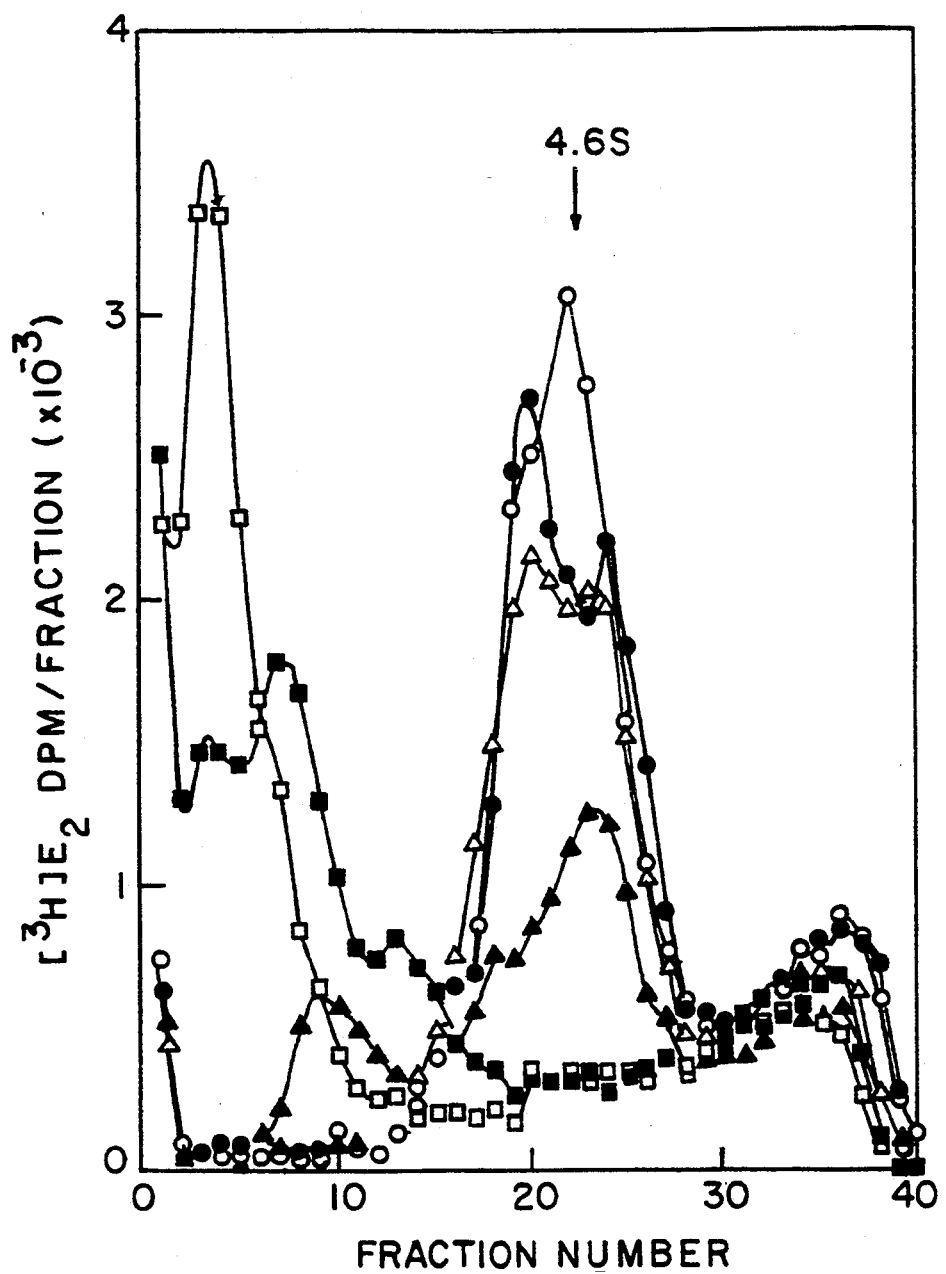
Figure 19:
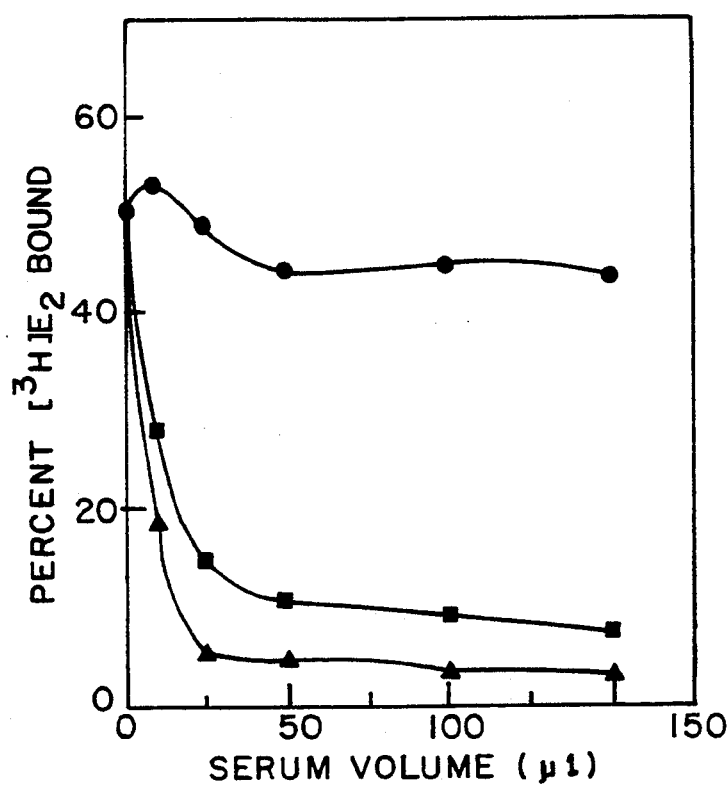
Figure 20:
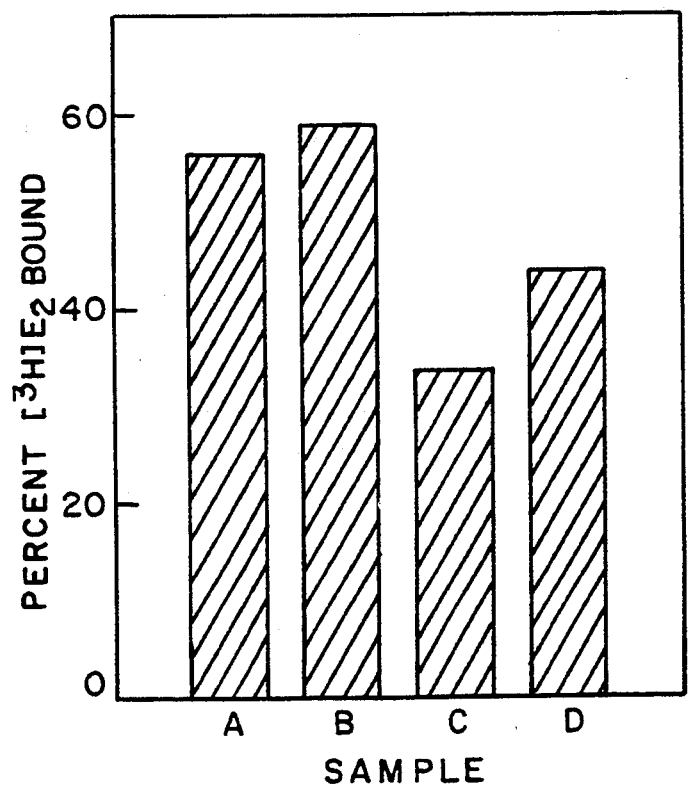

FIGS. 3A, 3B, and 3C are graphs illustrating the effect of antibody dilution on the sedimentation of ER using polyclonal antisera;

FIGS. 4A, 4B, and 4C are graphs illustrating the species specificity of rabbit polyclonal antibodies raised against human ER;

FIGS. 5A, 5B, 5C, and 5D are graphs illustrating the lack of cross-reactivity of human anti-ER polyclonal antisera with diverse steroid receptors;

FIG. 6 is a graph illustrating the interactions of human ER polyclonal antisera with 8S hormone receptor complexes;

FIG. 7 is a graph illustrating the interaction of human ER polyclonal antisera with 5S transformed ER protein;

FIGS. 8A and 8B are graphs illustrating the specificity of individual monoclonal antibodies raised against one immunogen;

FIG. 9 is a graph illustrating the ability of individual monoclonal antibodies to precipitate radiolabelled hormone/receptor complexes;

FIGS. 10A-10C are graphs illustrating the analysis of estrogen receptor interactions with individual monoclonal antibodies by sucrose density gradients;

FIGS. 11A-11D are graphs illustrating the site specificity of individual monoclonal antibodies as determined by sucrose density gradients;

FIGS. 12A-12E are graphs illustrating the interaction of individual monoclonal antibodies with radiolabelled hormone receptor complexes from various mammalian species;

FIGS. 13A-13D are graphs illustrating receptor specificity of individual monoclonal antibodies prepared against an oligopeptide from human ER;

FIGS. 14A-14C are graphs illustrating the interaction of two monoclonal antibodies with varying concentrations of radiolabelled hormone receptor complex;

FIG. 15 is a graph illustrating the interactions of one monoclonal antibody with unoccupied ER;

FIGS. 16A-16D are graphs illustrating the equilibrium binding of radiolabelled hormone receptor complex with monoclonal antibodies coupled to sepharose;

FIG. 17 is a graph illustrating the inhibition of binding of salt-activated 4S form and heat transformed 5S forms of estrogen receptors to DNA-cellulose;

FIG. 18 is a graph illustrating the analysis of polyclonal antisera binding to ER complexes previously activated by KCl;

FIG. 19 is a graph illustrating a dose-dependent inhibition of KCl-activated ER binding to DNA by polyclonal antisera; and FIG. 20 is a graph illustrating the binding of DNA to KCl-activated radiolabelled hormone receptor complexes in the presence of polyclonal antisera.

DETAILED DESCRIPTION OF THE PREFERRED EMBODIMENTS

The present invention as a whole is based upon the unique approach of developing site-specific polyclonal and monoclonal antibodies against the DNA-binding domain of estrogen receptor protein. The polyclonal antisera and the monoclonal antibodies are used to identify the presence of a DNA-binding domain within the ER under test and to differentiate between unactivated and activated states of estrogen receptor in vitro. On this basis the user is able to determine whether the DNA-binding domain of the ER is present in a functional or non-functional altered state; and whether the ER protein has been activated or not. The invention, therefore, includes specifically prepared immunogens; polyclonal antisera and monoclonal antibodies which bind specifically to the DNA-binding domain of ER; and immunoassays employing these site-specific antibodies with cellular samples on a functional and correlative test basis.

It will be noted and appreciated that the present invention overcomes several major impediments and advantages normally encountered in the production and use of specific antibodies. These include:

1. Since oligopeptides of known amino acid sequence are employed as the hapten within the prepared immunogen, there is no longer any need for purification of ER, particularly human ER, for immunization purposes; thus a task which normally requires large resources and considerable amounts of tissue is eliminated.

2. The present invention allows the user to select the precise domain intended to be the specific binding site for the antibody about to be produced. Previous approaches and techniques utilized either the whole estrogen receptor protein or the complete hormone/receptor complex as the immunogen neither of which provides any site specificity properties or capabilities whatsoever.

3. The polyclonal antisera prepared in the described manner bind to ER in the 8S, 4S, and 5S forms; in comparison, the monoclonal antibodies are able to distinguish between the 8S form and the 4S and 5S forms of ER.

4. The present invention precludes the binding of the site-specific monoclonal antibody to an ER protein when present in an altered, non-functional state unable to bind genomic DNA.

To fully appreciate the present invention, it is useful to focus on a single kind of estrogen receptor protein, recognizing that the characterization of the one ER may properly be extended to include all other types and sources of ER protein generally. For this reason, the remainder of this description and the experiments and empirical data which follow hereinafter are limited to the use of human estrogen receptor (hereinafter "hER"). For this purpose also, all the presently available information regarding the primary amino sequence and the various functional domains of human estrogen receptor protein have been employed. Nevertheless, it will be clearly and explicitly understood, that the scope of the present invention encompasses the ability to prepare site-specific antibodies against ER from all presently known sources and origins, whether human or animal.

Oligopeptides

As regards human ER protein and its functional states, it will be recalled that the human receptor molecule is a single polypeptide having 595 amino acids in sequence in which the DNA-binding domain (Region C) encompasses the amino acid segment at about positions 180-263 respectively. This domain is a critical region of the human ER because it provides the capability for the entire ER molecule to bind to genomic DNA in vivo. It is therefore this domain, the DNA-binding region, which must provide at least a portion of the amino acids in the oligopeptides which can serve as haptens for raising site-specific antibodies in accordance with the present invention.

As described in detail hereinafter, three oligopeptides having amino acid sequences identical to the amino acids at positions 201-215; at positions 231-245; and at positions 247-261 of human estrogen receptor ("hER") were prepared and purified. These individual oligopeptides were first linked to an antigenic protein carrier (such as keyhole limpet hemocyanin); and then were used as prepared immunogens to produce antibodies to the DNA-binding domain specifically. For purposes of practicing the present invention, however, it is not necessary that these specific hER amino acid sequences be employed when preparing the immunogen. To the contrary, for human purposes, it is required only that an oligopeptide be chosen whose amino acid sequence corresponds to at least one part of the entire 180-263 amino acid sequence which encompasses the C region of hER. Any amino acid segment able to function as a hapten (thereby providing one specific epitope or site-specific binding capability for the resulting antibody) is suitable for use. Moreover, although the characterized oligopeptides were approximately 15 amino acids in length, there is no requirement that any polypeptide chain conform to this length or size for purposes of preparing the immunogen. In general, however, it is desirable that the oligopeptide be at least in the order of from about 5-7 amino acids in length as the minimum segment size generally able to serve as a hapten. Nevertheless, any length of amino acids in sequence which is able to provide the necessary hapten function and site-specificity for the prepared immunogen is suitable and deemed to be within the scope of the present invention. In addition, although it is most desirable that the amino acid sequence of the oligopeptide be in fact identical to the true, naturally occurring amino acid sequence of the C region, this is not deemed to be an absolute requirement. It is expected that substantial variation of the amino acid sequencing differing from that found within the C region of the hER molecule is permissible; nevertheless, it is most desirable and most effective for the chosen amino acid sequence to be completely or very nearly identical to the C domain, particularly when the oligopeptide size is of minimal length.

Immunogens

Once the oligopeptide has been chosen, it is synthesized using conventional methods and chemically coupled to a protein carrier to form the prepared immunogen. The suitable protein carriers available for this purpose are conventionally known and available in great variety from diverse sources. The only requirements regarding the characteristics and properties of the carrier protein are: First, that the carrier be in fact antigenic alone or in combination with the oligopeptide; and second, that the carrier protein be able to present the chemically bound oligopeptide after administration in vivo such that antibodies specific against the DNA-binding domain of the ER molecule are produced. Clearly, as in the experiments described hereinafter, the preferred choice of protein carrier for immunization purposes was keyhole limpet hemocyanin (hereinafter "KLH"). However, any other carrier protein compatible with the host to be immunized is also suitable for use. Examples of such other carrier proteins include bovine serum albumin, gelatin, thyroglobulin, and the like.

Immunization Procedure

All immunizations and immunization procedures are performed in the conventionally known manner. It is expected that under certain use conditions, adjuvants will be employed in combination with the prepared immunogens. Alternatively, the prepared immunogens may be used alone and administered to the host in any manner which will initiate the production of specific antibodies.

In addition, the harvesting of polyclonal antiserum and the isolation of antibody containing sera or antibody producing cells follows the conventionally known techniques and processes for this purpose. Similarly, the preparation of hybridomas follows the best practices developed over recent years for this specific purpose [Marshak-Rothstein et al., *J. Immunol.* 122:2491 (1979)]. A complete detailed description of the preferred techniques and procedures are provided within the experimental section which follows hereinafter.

Polyclonal and Monoclonal Antibodies

Once obtained from their living hosts, the polyclonal antisera and the monoclonal antibodies should be evaluated and verified for their ability to bind specifically with the DNA-binding domain of the ER. The polyclonal antiserum prepared as described herein has been found to bind specifically with the C region of human ER in the 8S, 4S, and 5S forms. The polyclonal antisera therefore is able to identify the presence of human ER protein in its various states—be they the unactivated 8S form; the activated but untransformed 4S form; or the activated and transformed 5S form. When utilized within assay procedures for this purpose, these polyclonal antisera will accurately detect the presence of ER intracellularly; and will additionally provide the ability to identify the functional status of the detected ER protein. Within this context, a functional ER defines the ability of the estrogen receptor to bind to genomic DNA. Similarly, as empirically demonstrated hereinafter, monoclonal antibodies raised in the described manner are C domain specific binding antibodies and will bind only with the activated states of human ER be they transformed or untransformed. This corresponds to detecting hER in the 4S and the 5S forms only. The monoclonal antibodies are site-specific in their properties; and they will not and do not bind to the unactivated and untransformed 8S form of hER. Accordingly, the monoclonal antibodies will serve to identify both the functional status and activated state of the ER protein present within the cells or tissues being evaluated. Finally, when the polyclonal antisera and the monoclonal antibodies are employed within individual immunoassays to determine the presence of ER within a cellular sample, a direct comparison of the empirical results obtained using polyclonal antisera and monoclonal antibodies provides a direct and unequivocal measure of the functional status and activation state of the ER protein being detected.

Moreover, the ability to identify not only the functional status but also the activation state of human estrogen receptor in a cellular sample thus allows the use of assay procedures for the accurate quantitation of cytosolic estrogen receptors in breast cancer tissue samples. By employing the polyclonal antisera and the monoclonal antibodies within individual assays, the resulting data can be used to correlate not only the presence of estrogen receptor but also the quantity of functional receptor and its activation state within the tissue obtained from a single source or patient. On this basis, it now becomes possible to segregate breast cancers more accurately into two populations: those who are likely to respond to hormonal therapy; and those who are not likely to respond to hormones despite the presence of estrogen receptors because these are abnormal and non-functional in that person.

To demonstrate the uses of the polyclonal antisera and the monoclonal antibodies for such assay purposes, preferred protocols are provided which will illustrate the range of methods and manipulative steps able to be employed in the performance and the utilization of immunoassays. It will be expressly understood however, that the procedural steps described hereinafter are merely representative of the nature and manipulative steps employed within immunoassays generally. The described protocols are not self-limiting and are not restrictive to only the described manipulative steps and the test conditions employed. To the contrary, it is deemed and expected that a wide variety of homogeneous and heterogeneous immunoassay systems may be employed; that the parameters of concentration, volume, temperature, and choice of reagents can be varied extensively at will; that the identifying labels used with the polyclonal antisera and the monoclonal antibodies in such assays may be either isotopic or non-isotopic in nature; and that the protocols might be embodied as kits or other test apparatus in commercially saleable form rather than individually prepared reagents and reactants. The present invention presumes and incorporates by reference any conventionally known immunoassay techniques, procedures, protocols, substrates, and other non-decisive factors or parameters—all of which may be usefully employed within any given immunoassay procedure. None of these are deemed to be essential or dominant criteria when performing the methods of the present invention.

Accordingly, for illustrative purposes only, preferred protocols utilizing polyclonal antisera and monoclonal antibodies specific against the DNA-binding domain of human estrogen receptor are given hereinafter.

PREFERRED ESTROGEN RECEPTOR ASSAY PROTOCOL

Buffers

TEGM buffer consists of 10 mM Tris-HCl; 1 mM ethylenediamine tetracetic acid (EDTA); 10% vol/vol glycerol; 10 mM sodium molybdate; 10 mM monothioglycerol; and 0.02% sodium azide (pH 7.4 at 2° C.)

Preparation Of Cytosol Fractions

Human breast cancer tissue is pulverized, weighed, and placed in a test tube on ice. Unless otherwise stated, all manipulations are carried out at 0°–4° C. Ice cold TEGM buffer is added to the tissue in a 4:1 vol/wt and homogenized with a polytron Pt-10 using 5 sec. bursts and 30 sec. cooling periods in between bursts. The homogenate is then transferred into ultracentrifuge tubes; and the homogenate is centrifuged at 100,000 × gravity for 45 minutes to obtain the high speed supernatant or cytosol. The cytosol is transferred to a clean tube and placed on ice.

Preparation Of Radioactive Estradiol Stock Solutions

[$^3$H] estradiol is obtained in solution of benzene/ethanol. Aliquot is removed and dried under nitrogen. The dried material is resuspended in a small volume (2–5 ul) of ethanol; buffer is then added to dissolve the radiolabelled estradiol. The concentration of the estradiol [$E_2$] is then determined by conventional radioactive counting.

Incubation Of The Cytosol With Radiolabelled Estradiol

Aliquots of the cytosol are then incubated with 5 nM of radiolabelled estradiol at 0° C. for 16 hours to form the estrogen receptor/estradiol complexes. To determine the nonspecific binding, parallel aliquots of cytosol were incubated with [$^3$H]$E_2$ and a 100 fold molar excess of unlabelled diethylstilbestrol.

Removal Of Free Radioactive Estradiol With Dextran Coated Charcoal ("DCC")

The DCC suspension in TEGM buffer is centrifuged and the supernatant is discarded. The cytosol incubation is then transferred into the DCC pellet and mixed and kept on ice for 20 minutes with intermittent mixing. The suspension is then centrifuged at 1,000 × gravity for 10 minutes and the supernatant is used as a source of labelled cytosol.

Determination Of Estrogen Receptors By An Enzyme Immunoassay

Microtiter 96-well plates are used. Aliquots of bovine serum albumin conjugated oligopeptide (10 ng/well) in 50 ul of phosphate buffered saline are pipetted into each well and allowed to bind at 0° C. for 16 hours. The wells are then coated with 200 ul of 2% bovine serum albumin (BSA) in phosphate buffered saline (PBS) for 1–2 hours at 25° C. The plates are then washed with PBS three times and used for competitive binding assay.

An aliquot of the desired antibody (monoclonal or polyclonal) is diluted 1:2,000 with BSA/PBS and 50 ul are incubated for 16 hours at 0°–2° C. with increasing volumes of the human breast tissue cytosol (10–200 ul). This allows the antibody receptor interaction to form the antigen antibody complex. The antibody/cytosol mixture is then added to the wells of the microtiter plate and incubated at 0°–2° C. for an additional 16 hours. The individual wells are then washed three times with PBS; and a secondary antibody previously conjugated to alkaline phosphatase is added in 1:5,000 dilution in BSA/PBS to each well and the reaction mixture incubated at 25° C. for 2 hours. The unbound antibody is then removed and the wells washed three times in PBS.

An enzyme substrate for alkaline phosphatase is then added to each well and incubated at 25° C. for 30 minutes in the dark. The color reaction is then stopped by addition of 0.5 N NaOH. The color product of the reaction is measured by ELISA microtiter reader at 450 nm.

Control incubations are made in the absence of cytosol. This allows measurement of all the antibody bound in the reaction mixtures. Nonspecific binding is determined by omitting the primary antibody. Additional controls are provided by wells that were coated with BSA only and do not contain any oligopeptide. Calf uterine cytosol with known estrogen receptor content is used as external standard to evaluate the reproducibility of the assay.

Determination Of The Functionality Of The Human Estrogen Receptor

An aliquot of the cytosol to be tested is labelled with radioactive estradiol as described above and is incubated with 25 ug of the antibody at 0°-2° C. for 4–16 in the presence of 0.4 M KCl. The total sample is then layered together with $^{14}C$-labelled BSA and human gamma-globulin using a 5–20% sucrose density gradient (made in TEGM buffer containing 0.4 M KCl, in 4 ml polyallomer ultracentrifuge tubes). The gradients are centrifuged at 50,000 rpm in a SW60 Beckman rotor for 18 hours at 2° C. The gradients are then fractionated into 0.1 ml individual fractions, 0.5 ml of water and 4 ml of Liquiscint are then added and the samples are then counted for radioactivity. The intact estrogen receptor binds to the antibody and sediments in the 7-8 S region of the gradient. Estrogen receptors with defective, missing, or altered DNA binding domain will not interact with antibody and therefore will sediment as 4-5 S estrogen receptor complexes.

To further document and demonstrate the individual parts of the present invention and the major advantages and abilities provided by the invention as a whole, a variety of different experiments were performed and the resulting data recorded. These empirical experiments and data are provided in detail hereinafter in order that the properties, characteristics, uses, and advantages of each component part may be properly appreciated and understood. It will be recalled, however, that these experiments are directed to only human estrogen receptor; and that the specific embodiments, procedures, modes of preparation, and immunoassays performed are merely illustrative and representative of the totality of embodiments encompassed within the scope of the present invention.

I. Preparation Of Synthetic Oligopeptides and Immunogens Representative Of The DNA-Binding C Domain Of Human Estrogen Receptor Protein The DNA-binding region of human estrogen receptor (hER) is encompassed by the amino acids at positions 180-251 in the native protein [Green et al., *Nature* 320:1345 (1986)]. FIG. 1 depicts the amino acid sequence of the DNA-binding domain termed the "C" region and of the three oligopeptides chosen as haptens and immunogens to obtain specific antisera. It will be noted that:

Peptide No. 1 represents the segment of amino acids from positions 201-215 within native hER as
Ac-Ser-Cys-Glu-Gly-Cys-Lys-Ala-Phe-Phe-Lys-Arg-Ser-[$^3H$]Ile-Gln-Gly-NH$_2$;

Peptide No. 2 represents the segment of amino acids from positions 231-245 within native hER as
Ac-Lys-Asn-Arg-Arg-Lys-Ser-Cys-Glu-[$^3H$]Ala-Cys-Arg-Leu-Arg-Lys-Cys-NH$_2$; and Peptide No. 3 represents the segment of amino acids from positions 247-261 of the estrogen receptor protein as
Ac-Glu-Val-Gly-Met-Met-Lys-Gly-[$^3H$]Ile-Arg-Lys-Asp-Arg-Arg-Arg-Gly-NH$_2$;
wherein Ac is an acetyl moiety.

Cumulatively, therefore, the three peptide sequences are identical to about 70% of the total "C" binding domain of human ER. The nine conserved cystein residues believed to play a role in the tertiary structure of the putative zinc-binding fingers are noted by asterisks within FIG. 1.

Synthesis Of Oligopeptides

The oligopeptide Nos. 1, 2, and 3 were prepared using conventionally known solid phase peptide synthesis methods [Merrifield, R.B., *J. Am. Chem. Soc.* 85:2149 (1963)]. Once synthesized, the individual oligopeptides were purified by gel filtration and analyzed for purity by HPLC. Analysis of the amino acid composition correlated well with the primary sequence. Each peptide contained one [$^3H$]-labelled amino acid as a tracer. This provided the means for determining the efficiency of coupling to the various carrier proteins.

REAGENTS

Isotopes and Chemicals

[6,7$^3H$]estradiol (40–60 Ci/mmol) ([$^3H$]E$_2$), 7d,17α-dimethyl [17α-methyl $^3H$]-19-nortestosterone (70–85 Ci/mmol) ([$^3H$]DMNT) 16α-ethyl-21-hydroxy-19-nor [6,7$^3H$]-pregn-4-ene-3,20-dione (40–60 Ci/mmol) ([$^3H$]ORG 2058), [$^3H$]-triamcinolone acetonide (20–40 Ci/mmol) ([$^3H$]TA), unlabelled DMNT, and ORG 2058 were obtained from Amersham, Arlington Heights, Ill. Unlabelled TA was obtained from Sigma Chemical Co., St. Louis, Mo., unlabelled diethylstilbestrol (DES) and E$_2$ were obtained from Steraloids, Wilton, N.H. All other chemicals were reagent grade and were obtained from commercial sources.

Buffers and Solutions

Buffer TGT: 50 mM Tris-HCl, 10% glycerol, 10 mM thioglycerol (pH 7.4 at 2° C.);.

Buffer TGT/MO: buffer TGT with 10 mM sodium molybdate.

Buffer TT: 50 mM Tris-HCl, 10 mM thioglycerol (pH 7.4 at 2° C.)

Buffer TT/KCl: buffer TT containing 0.4 M KCl.

Coupling Of Oligopeptides To Carrier Proteins

To prepare effective immunogens, the oligopeptide Nos. 1, 2, and 3 were individually coupled to known carrier proteins to form antigenic immunogens. The carrier proteins of choice were keyhole limpet hemocyain (hereinafter "KLH") and bovine serum albumin (hereinafter "BSA"). The KLH-coupled peptides were used as immunogens while the BSA-coupled peptides were used only for screening assays. This coupling procedure was performed as follows.

KLH and BSA were dissolved in phosphate buffered saline (PBS: 0.2 g KH$_2$PO$_4$, 8 g NaCl, 2.16 g Na$_2$HPO$_4$ 7H$_2$O in one liter of distilled water, pH 7.5) to give a final concentration of 1 mg/ml. One hundred mg of each peptide was then dissolved in 10 ml of KLH solution and 50 mg of each peptide was dissolved in 5 ml of BSA solution. The pH of the mixtures was adjusted to 9 with 0.1 M LiOH. The coupling of the peptides to the carrier proteins was initiated by dropwise addition of 6.25% glutaraldehyde to achieve a final concentration of 1% glutaraldehyde. Each mixture was then incubated at 0°–4° C. for 1 hour with gentle agitation. Aliquots (50–200 ul) were then removed and used to determine total peptide concentration by radioactivity counting. The remainder of each mixture was then transferred to dialysis tubes and dialyzed extensively against four changes of PBS. Aliquots were then removed after dialysis and counted to determine the efficiency of coupling. The remaining dialyzed material was divided into 1 ml aliquots and frozen at $-80°$ C. until needed.

II. Use Of Oligopeptide Immunogens To Obtain Polyclonal And Monoclonal Antibodies Against The DNA-Binding Domain Of hER Immunization New Zealand white female rabbits (7–9 lbs) were obtained from Pine Acre Rabbitry, Norton, Maaa. Prior to immunization serum was collected from each rabbit by bleeding through the ear artery and designated as preimmune serum. One day later each animal was injected subcutaneously at multiple sites along the back with a total of 1 ml of an emulsion made by mixing equal volumes of complete Freund's adjuvant and KLH-conjugated peptide mixture. The final emulsion contained 1 mg/ml of the desired peptide. After three weeks the rabbits were boosted with the antigen in incomplete Freund's adjuvant. Two weeks after the booster shots the rabbits were bled and the sera were collected and tested for the presence of peptide-specific antibodies by enzyme-linked immunosorbent assay (ELISA). The animals were then given booster shots several times and bled 14 days after the final booster. This procedure provided all the peptide-specific polyclonal antisera described hereinafter.

In addition, three groups (5 animals/group) of female mice [(BALB/cA/J)F$_1$] 6–8 weeks old were also immunized by injecting s.c. 100 ug of the designated oligopeptides, emulsified in Freund's complete adjuvant. Two s.c. booster injections were given at 3 week intervals. The mice were bled through the vein and the sera were tested for antibodies by sucrose density gradient analysis. Those mice which appear to have antibodies against ER were then selected. After one month of rest the mice were given 100 ug of the antigen in PBS intraperitoneally (i.p.) and sacrificed three days later; subsequently, their spleens were removed and used for cell fusion and the production of monoclonal antibodies specific for the C-binding domain of human ER.

Preparation Of Hybridomas And Isolation Of Monoclonal Antibodies

Cell fusion was carried out by the method of Marshak-Rothstein et al. [*J. Immunol.* 122:2491 (1979)]. Briefly, mouse spleens were excised; the fat and mesenteric tissues were removed quickly; and a single cell suspension was made by squeezing the spleen between two glass slides in Hank's balanced salt solution (HBSS) buffered with 0.01 M phosphate, pH 7.2. Red blood cells were lysed by brief incubation in ammonium chloride lysis buffer. Spleen cells ($5\times10^7$ cells) were mixed with Sp 2/0 cells ($5\times10^6$ cells) in round bottom tubes and pelleted at $700\times g$ for 5 min at 22° C. The cells were resuspended in serum-free DME and centrifuged. After removal of the supernatant the cell pellet was resuspended for six minutes in 0.5 ml of polyethylene glycol 1,500 ("PEG", 30% v/v) (Baker Chemical, Co., Phillipsbur N.J.), followed by addition of 4 ml of serum free DME (Dulbecco's Modified Eagle's Medium) to dilute out the PEG. The cell suspensions were transferred into petri dishes ($100\times17$ mm) and DME containing 20% FCS (fetal calf serum) was added and the cultures were kept at 32° for 24 h under 5.6% $CO_2$. The cells were then pelleted and resuspended in HAT (hypoxanthine, aminopterin, and thymidine) conditioned medium ($1\times10^6$ cells/ml). Aliquots of the cell suspension (0.1 ml) were dispensed into 96-well flat bottom microtiter dishes and incubated at 37° C. Seven days later the hybridoma cells were treated with 0.1 ml of conditioned media (DME, HT). After another two days, the resulting hybridomas were screened by enzyme-linked immunosorbent assay (ELISA) against BSA-conjugated oligopeptides.

The isotype of each monoclonal antibody was determined by ELISA. Microtiter plates coated with the immunogenic oligopeptide were incubated with aliquots of the spent media from the hybridoma. Bound antibody heavy chain class was determined by addition of goat-antimouse isotyping reagents (Southern Biotech, Birmingham, Ala.) diluted 1:1,000 in PBS-0.2% BSA, followed by alkaline phosphatase conjugated rabbit-antigoat secondary antibody and the substrate.

Hybridoma clones that tested positive by ELISA were recloned by limiting dilution. Cells were diluted to 1, 0.3, and 0.1 cell equivalent/ml in DME containing 20% FCS and BALB/c peritoneal exudate cells ($5\times10^4$ cells/ml) and then plated in 96-well microtiter plates. After ten days, wells with single hybridoma clones were by microscopic examinations and tested for presence of antibodies by ELISA. Clones that tested positive were expanded in large flasks, spent media were collected, and cells were either used for ascites productions or frozen for later use.

III. Properties And Characteristics Of DNA-Binding Domain Specific Anti-Human ER Polyclonal Antisera Positive antisera were obtained from all six rabbits, with varying titer. Within this detailed description, the individual peptide specific polyclonal antisera obtained against peptide No. 1 will be referred to as either ATIA or ATIB since each antiserum was individually obtained from only one rabbit and was never mixed with any other antiserum. Similarly, polyclonal antisera raised against peptide No. 2 will be identified as AT2A and AT2B respectively; and polyclonal antisera specific for peptide No. 3 are individually designated as AT3A and AT3B. The properties, specificity, titer, and other characteristics were then empirically evaluated.

EXPERIMENTAL SERIES 1:

The Binding Of Rabbit Polyclonal Anti-ER Antibodies To hER

Sources Of Tissue

Human breast cancer tissue was obtained through the Steroid Receptor Assay Laboratory of Boston University. Tissue procurement was performed as described in Muller et al., *Cancer Res.* 40:2941 (1980). Calf uterine tissue was obtained from a local slaughter house as described previously [Traish et al., *Endocrinology* 118:1327 (1986)]. Rat uterine tissue was obtained from 21–23 day old female Sprague-Dawley CD rats. Rat prostates were obtained from mature 24h castrated males (charles River Breeding Laboratories).

Cytosol fractions from each kind of tissue were prepared in buffer as described previously [Traish et al., *Endocrinology* 118:1327 (1986)]. Briefly, fresh tissue or frozen tissue powder was homogenized (1 g/4 ml) in buffer TT, pH 7.4 at 2° C. The homogenate was then centrifuged at 105,000×g for 45 min. at 2° C. and the supernatant fraction (cytosol) was used for receptor binding studies.

Labeling Of Cytosols With Steroid Hormones

To label the ER aliquots of the calf or human breast tissue cytosols were incubated at 2° C. for 4 h with 5 nM [$^3$H]E$_2$ in the absence (total binding) or presence (non-specific binding) of a 100 fold molar excess of unlabelled DES. Progesterone receptors were labelled by incubating calf uterine cytosol with 15 nM [$^3$H]ORG2058 in the absence or presence of unlabelled ORG2058 as described previously [Traish et al., *Steroids* 47:157 (1986)]. Androgen receptors were labelled by incubating rat prostatic cytosol with 10 nM [$^3$H]DMNT in the absence or presence of unlabelled DHT. Glucocorticoid receptors were labelled by incubating calf uterine cytosol with 10 nM [$^3$H]TA and 20 nM unlabelled ORG2058 in the absence or presence of unlabelled TA as described previously. At the end of the incubation free radioactivity was removed with dextran coated charcoal pellets and the supernatant used for antibody-receptor interactions.

Sucrose Density Gradient Analysis

Sucrose density gradients (8–30%) were prepared in TT buffer containing 0.4 M KCl. In some experiments (as indicated) the gradients were made 8–30% in TT buffer containing 10% glycerol with or without 0.4 M KCl. Samples to be analyzed were layered on the gradient together with $^{14}$C-labelled sedimentation markers. The gradients were centrifuged at 50,000 rpm in an SW60 rotor for 18 h at 2° C. Gradients were fractionated into individual 0.1 ml fractions, scintillation fluid was added, and radioactivity counted.

Binding Of Rabbit Polyclonal Anti-ER Antibodies To Human Estrogen Receptors

Human breast tissue cytosol (4–8 mg protein/ml) was prepared and labelled with [$^3$H]E$_2$ for 90 min at 0° C. To determine non-specific binding cytosol was incubated with 5.7 nM [$^3$H]E$_2$ and 2 uM unlabelled diethylstilbestrol. At the end of the incubation, samples were treated with DCC pellets at 0° C. for 20 min. After centrifugation aliquots of the supernatant (0.2 ml) containing [$^3$H]RE$_2$ complexes were further incubated at 0° C. for 4 h with 0.1 ml of the indicated sera. Samples were then analyzed on sucrose density gradients as described. The results are given by FIG. 2 in which serum AT1A is represented by open circles; AT1B by solid circles; AT2A by open triangles; AT2B by solid triangles; AT3A by open squares; and AT3B by solid squares).

Figure 2:
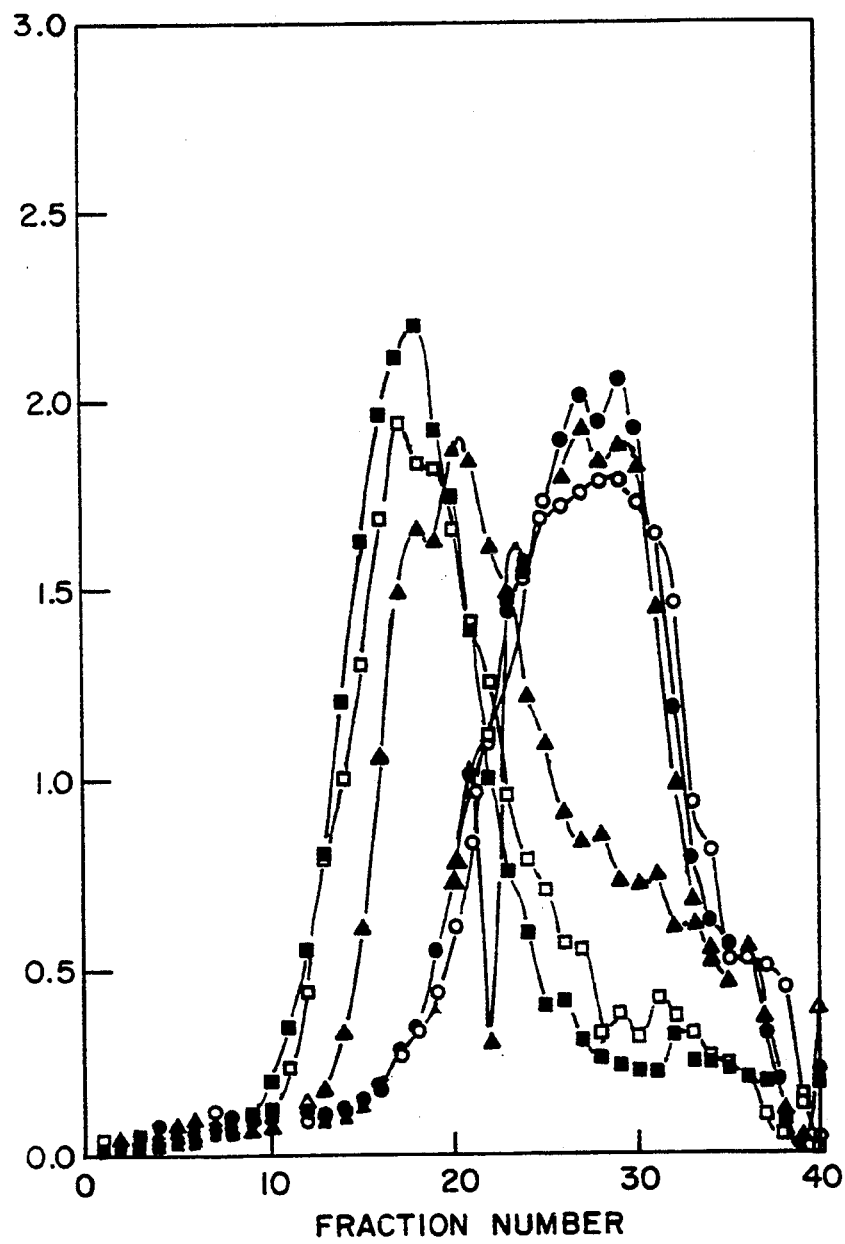
FIG. 2 is a graph illustrating sucrose density gradient analysis of the binding of rabbit polyclonal anti-ER antibodies to human estrogen receptors.

One purpose of this study was to determine if these polyclonal antibodies individually recognized not only the denatured hER receptor but also the "native" form of hER. The data in FIG. 2 show that antisera AT1A and AT1B did not interact with native ER since these sera did not increase the sedimentation coefficient of ER. AT2A antisera recognized the native form of ER as demonstrated by the increase in the sedimentation coefficient of ER, whereas serum AT2B did not, although both animals were immunized with the same peptide. Antisera AT3A and AT3B caused an increase in the sedimentation coefficient of ER suggesting that both antisera contain antibodies which recognize the native form of ER. Preimmune sera from all animals failed to cause any significant shift in the profile of ER sedimentation. These data clearly show that antisera raised against peptide No. 2 and 3 contain antibodies to the predetermined regions of ER.

Effect Of Antibody Dilution On The Sedimentation Of ER

To estimate the titer of these antisera by sucrose density gradient analysis, [$^3$H]RE$_2$ was incubated with various dilutions of the antisera. Human breast tissue cytosols were labelled as described above and then incubated with the antisera AT3A and AT3B at 10, 50, and 100 fold dilutions. After incubation for 4 h at 0° C. samples were analyzed on sucrose gradients. The results are presented by FIG. 3 in which the left panel represents AT3A and the right panel AT3B. (Open circles represent control, open triangles upward 10 fold, open squares 50 fold, and downward triangles 100 fold dilution.) As shown in FIG. 3, all three antisera (AT2A, AT3A, AT3B) recognized ER in its native form even at 1:100 dilutions. Antiserum AT2A appears to have the lowest titer and AT3B the highest titer.

EXPERIMENTAL SERIES 2:

The Specificity Of Rabbit Polyclonal Anti-ER Antibodies

Species Specificity Of Rabbit-Polyclonal Antibodies Against Human ER

Since the oligopeptides were synthesized according to the published sequence of the human ER, it was important to determine the specificity of these antibodies. Accordingly, tissue cytosols (5–7 mg protein/ml) from human breast cancer, calf uterus, and rat uterus were prepared and labelled with [$^3$H]E$_2$ as described herein. Aliquots of the DCC-treated cytosol were then reincubated at 0° C. for 4 h with the three antisera. Samples were then analyzed on sucrose density gradients. The results are given by FIG. 4 in which the open circles represent control; solid circles indicate AT2A; open triangles identify AT3A; and solid triangles designate AT3B.

FIG. 4 shows the results of incubation of [$^3$H]-labelled ER from calf uterine cytosols (middle panel), and rat uterine cytosols (right panel), and human breast cancer tissue cytosols (left panel) with the three antisera. All three antisera recognized ER from the various species, albeit, with less affinity for the rat uterine ER.

Absence Of Cross-Reactivity Of Human Anti-ER Polyclonal Antibodies With Steroid Receptors It is generally recognized that steroid hormone receptors have similar functional domains. One of these domains represents the putative "C" region, DNA-binding domain of the receptor. It has been suggested that this region is likely to be conserved among the various steroid receptors [Evans, R.M., *Science* 240:889 (1988)]; furthermore, this region is thought to have the conserved cysteine and histidine residues which may be involved in the formation of the zinc-finger-like structures of the proteins [Adler et al., *Cell* 52:685 (1988); Weinberger et al., *Nature* 318:670 (1985)]. Those reported observations would suggest that polyclonal antibodies raised against a preselected C-domain spanning the DNA-binding region of human estrogen receptor would cross-react with other steroid hormone receptors. To demonstrate the erroneous nature of this premise cytosols from calf uterine tissue were labelled with [$^3$H]E$_2$, [$^3$H]ORG2058, and [$^3$H]TA to form [$^3$H]ER, [$^3$H] progesterone receptor (PgR), and [$^3$H]-glucocorticoid receptor complexes (GR). Similarly, cytosols from rat prostates were labelled with [$^3$H]DNMT to form [$^3$H] androgen receptor complexes (AR).

More specifically, calf uterine cytosol was prepared and labelled with 5 nM [$^3$H]E$_2$ in absence or presence of 2 uM DES; similar aliquots were incubated with 10 nM [$^3$H]ORG2058 in absence or presence of 2 uM ORG2058. To label the glucocorticoid receptor, cytosols were incubated with [$^3$H]TA and unlabelled ORG2058 in absence or presence of unlabelled TA. Rat prostate cytosol was labelled with [$^3$H]DMNT in absence or presence of unlabelled DHT. All samples were then incubated at 0° C. for 16 h; treated with DCC pellets; and the bound steroid receptor complexes separated by centrifugation. The supernatants were then incubated at 0°–4° C. for 4 h with the three individual antisera and subsequently analyzed on sucrose density gradients. The results are given by FIG. 5 in which the open symbols represent control and the solid symbols represent addition of polyclonal antibodies. Clearly, the data in FIG. 5 demonstrate that none of the three individual polyclonal antisera cross-reacted with PgR, GR, or AR, but all of them did react with ER.

EXPERIMENTAL SERIES 3:

Interactions Of Rabbit Polyclonal Human ER Antibodies

Interactions Of Human ER-Antibodies With the 8S Hormone Receptor Complexes

In cell free systems the solubilized ER can be found as 8S complexes (unactivated, untransformed), 4S complexes (activated but untransformed), or 5S complexes (activated and transformed). It has been reported that the DNA-binding region is inaccessible to DNA in the 8S form of the receptor [Muller et al., *J. Biol. Chem.* 258:9227 (1983)] and that DNA binding requires activation and/or transformation of the receptor [Bailey et al., *J. Biol. Chem.* 255:2729 (1980)]. To test if the DNA binding, C-region in the 8S receptor complex is also inaccessible to antibodies, [$^3$H]labelled ER complexes were incubated at 0° C. with antiserum AT3B.

For this purpose, calf uterine cytosol was prepared in low salt buffer and labelled with [$^3$H]E$_2$ in absence or presence of unlabelled DES as described previously herein. After removal of free steroids with DCC, samples were incubated with the antisera for 4 h at 0° C. and then analyzed on sucrose density gradients prepared in low salt buffer. The results are given by FIG. 6 in which the open circles represent control; solid circles antiserum AT2A; open triangles antiserum AT3A; and solid triangles antiserum AT3B. The analysis on SDG in low salt buffer showed that the antiserum AT3B bound to ER even in the 8S state. This shows that the DNA-binding region is accessible to antibody interaction.

Interaction Of The Human ER Polyclonal Antibodies With The 5S Transformed ER

To evaluate further the binding of these polyclonal antibodies to the untransformed ER, the sedimentation profiles of ER prepared in the absence or presence of molybdate which were then treated with the different antisera were evaluated. All three antibodies recognized ER in the absence or presence of sodium molybdate (data not shown) suggesting that the antibodies bound even to unactivated (8S) ER. The binding of the antisera to the activated and transformed (5S) receptor complexes was then examined.

Calf uterine cytosol was prepared in TGT buffer without molybdate. The cytosol was incubated at 0° C. for 90 min with 5 nM [$^3$H]E$_2$ in absence or presence of unlabelled DES. Samples were then incubated at 28° C. for 30 min to induce heat transformations of ER. The samples were placed on ice and free steroids were removed with DCC. Aliquots of these incubations were then mixed with the indicated antisera and kept at 0°–4° C. for 4 h. Samples were then analyzed on sucrose density gradients containing 0.4 M KCl. The results are presented by FIG. 7 whose symbols are identical to those employed earlier in FIG. 6.

As shown in FIG. 7, the 5S ER antibody complexes sedimented as larger complexes than did 5S ER alone. These empirical results demonstrate that the antibodies had recognized the "C" region; and furthermore, they indicate that the C-domains recognized by the antibodies are not involved in the dimerization of ER. Finally, to determine if these antibodies recognize the unoccupied ER, unbound ER was incubated with the immune sera for 4 h at 0° C. Subsequent analysis on SDG containing 0.4 M KCl, and postlabelling of the fractions with [$^3$H]E$_2$, demonstrated the binding of [$^3$H]E$_2$ to complexes sedimenting in the 7–8S regions of sucrose gradients.

The IgG Class Of Antibody Comprising The Polyclonal Human ER Antisera

To identify the class of antibody comprising the ATA1, ATA2, and ATA3 antisera, an immunoprecipitation assay was performed as follows.

Aliquots of cytosol labelled with [$^3$H]E$_2$ were incubated with the specified antisera for 4 h at 2° C. The antibody receptor complexes were then immunoprecipitated by addition of 200 ul of goat antirabbit-IgG linked to agarose (ICN Biochemicals). The incubations were continued overnight at 2° C. with constant agitation. The agarose resin was then collected by centrifugation; washed with ice cold buffer (4×5 ml) by resuspension and recentrifugation; and the bound radioactivity then extracted with absolute ethanol and counted. Controls were carried out by incubating the receptor protein with preimmune sera or by incubating ER in the absence of antisera. The specifically bound radioactivity was corrected for nonspecific receptor adsorption to the agarose resin; and the immunoprecipitated ER was estimated.

Empirical analysis showed that all three antisera immunoprecipitated ER showing that the antibodies are of the IgG class since the secondary antibody conjugated to agarose was against rabbit IgG.

IV. Properties And Characteristics Of C-Domain Specific Anti-Human Monoclonal Antibodies (MAbs)

EXPERIMENTAL SERIES 4:

Specificity Of Anti-hER Monoclonal Antibodies

Assay Of Mouse Antisera Prepared Against Synthetic Peptide No. 3 Conjugated To KLH Antisera from immunized BALB/c A/J F1 mice were first tested for their ability to increase the sedimentation of ER in SDG containing 0.4 M KCl. Only antisera from mice immunized with oligopeptide No. 3 (amino acids 247–261) tested positive against native estrogen receptor (data not shown). Because our goal was to screen for antibodies that recognize the native ER, only those animals with positive anti-sera against the native ER for development of monoclonal antibodies.

ELISA Assay Of Monoclonal Antibodies Prepared Against Synthetic Peptide No. 3 Conjugated To KLH After cell fusion, the tissue culture supernatants from the various clones were initially screened for monoclonal antibodies (hereinafter MAb) against the oligopeptide conjugated to BSA (No. 3-BSA). Fifteen clones appeared to contain MAbs against the oligopeptide No. 3. To determine if the clones secreted immunoglobulins against the oligopeptide, the spent tissue culture media from each clone was assayed by ELISA for presence of antibodies. The assay was performed as follows.

Aliquots (50 ul) of the bovine serum albumin conjugated peptide (3 ug/well) in PBS were dispersed into the microtiter wells and incubated at 0°–4° C. for 16–20 h. The plates were then blocked with 2% BSA in PBS and used to screen the tissue culture supernatants from the various hybridoma clones. Tissue culture supernatants of various dilutions from fusion No. 1 or fusion No. 2 were added to microtiter plates in a final volume of 50 ul and incubated at 0°–4° C. for 16 h. The plates were then washed and the antibody binding activity was determined by alkaline-phosphatase activity conjugated to rabbit antimouse antibody. Mouse polyclonal antiserum against polypeptide No. 3 was used as a control (MS). The results are given by FIG. 8, in which panel A illustrates fusion No. 1; data and panel B illustrates fusion No. 2 data. Clearly, the data demonstrates the specific binding of monoclonal antibodies from individual hybridomas to the oligopeptide No. 3 coupled to BSA.

Immunoprecipitation Of [$^3$H]RE$_2$ With Monoclonal Antibodies Prepared Against Oligopeptide AT3

Initially, female mice (BALB/cxA/J) F$_1$ were injected IP with pristane (0.5 ml) and seven days later the animals were injected with $1 \times 10^6$ hybridoma cells in 0.2 ml PBS. Ascitic fluid was collected 7–10 days later by insertion of a needle into the peritoneal cavity. The ascitic fluid was then clarified by centrifugation at 700$\times$g for 10 min, divided into several vials, and kept frozen at $-70°$ until use.

Aliquots of [$^3$H]E$_2$-labelled cytosol prepared as previously described were treated with DCC and then incubated at 0°–4° C. for 16 h with normal mouse serum (NMS, 10 ul), serum from mice immunized with oligopeptide No. 3 (mouse immune serum, 10 ul), ascitic fluid (10 ul) derived from hybridoma clones No. 33, 36, 31, 35, 110, 320, and 318 and spent tissue culture media (200 ul) from clones No. 51, 52, 114, 213, 16, 67, and 48. The formed [$^3$H]RE$_2$ complexes were then precipitated by addition of 250 ul of rabbit antimouse Ig and incubation for 6 additional hrs at 2° C. The precipitated material was collected by centrifugation and washed three times with PBS. The protein-bound radioactivity was extracted with ethanol and counted. All data points were corrected for non-specific binding and plotted as % of specific [$^3$H]RE$_2$ added to each sample. The results are given by FIG. 9. Clearly, the assay of these antibodies for their ability to bind [$^3$H]RE$_2$ by immunoprecipitation showed that clones No. 33, 36, 35, 114, 213, 16, and 318 recognized the native ER molecule.

Analysis Of Estrogen Receptor Interaction With Monoclonal Antibodies Produced Against Oligopeptide No. 3 By Sucrose Density Gradients Calf uterine cytosol was prepared in buffer TGET/MO and labelled with [$^3$H]E$_2$ at 0° C. for 4 h. To determine non-specific binding aliquots were labelled with [$^3$H]E$_2$ in the presence of 5 uM unlabelled DES. At the end of the incubation, free radioactivity was removed with dextran-coated charcoal pellets and samples were removed and placed in propylene microfuge tubes. Aliquots (50–100 ug equivalent of the antibody) of the ascites fluid from the various clones were then added and the samples were reincubated at 0° C. for 16 h. Additional samples were treated either with an equimixture of ascites from four clones or remained untreated (control). Samples were then analyzed on 5–20% sucrose density gradients made in TGET/MO buffer containing 0.4 M KCl as described in the methods. All data presented are corrected for non-specific binding. The arrows represent the sedimentation of the $^{14}$C-labelled protein markers included in each gradient. The results are given by FIGS. 10A–10C respectively.

As shown in FIG. 10A, of the clones tested for their ability to increase the sedimentation coefficient of ER by SDG, only four (No. 16, 33, 114, and 213) bound to ER with high affinity as demonstrated by the increased sedimentation of ER from 4–5S to 7S in the presence of 0.4 M KCl (non-equilibrium conditions). Seven of the MAbs (16, 33, 114, 213, 35, 36, and 318) immunoprecipitated the native ER (FIG. 9). Three of these (36, 35, 318) recognized the native ER complex albeit with low affinity, since they do not cause significant change in the sedimentation of the native ER on SDG (FIGS. 10B and 10C). All but one of these MAbs (No. 67, IgM) were of the IgG1 class.

Moreover, as shown in FIG. 10A, MAbs No. 213, 114, 33, and 16 were of high affinity and presumably bound to the same epitope on ER complexes. This conclusion is based on the empirical observation that an equal mixture of these antibodies did not result in an additional increase in the sedimentation of ER when compared to the increase obtained by anyone of these MAbs. These results also suggest that the 4 MAbs are site specific. This premise was empirically validated and confirmed below.

Site Specificity Of The Monoclonal Antibodies As Determined By Sucrose Density Gradients The conclusive premise was tested by incubating [$^3$H]RE$_2$ with MAbs alone or with MAbs preincubated with 50 ug of oligopeptide No. 3. Experimentally, calf uterine cytosol was prepared and labelled as described previously. Aliquots of the monoclonal antibodies to be tested (100 ug) were first incubated at 0° C. for 5 h in the absence (control) or presence of a 100 ug of oligopeptide No. 3 in PBS or with an aliquot of calf uterine estrogen receptor complexed to unlabelled E$_2$ (200 fmol). At this point, all samples received an aliquot of the [$^3$H]E$_2$-labelled cytosol and kept at 0° C. for 16 h. Antibody-receptor interactions were analyzed by SDG as described earlier. The results are presented by FIG. 11 in which panel A represents MAb No. 213, panel B No. 33, Panel C No. 114, and panel D No. 16. Open circles indicate sedimentation of [$^3$H]RE$_2$ only; solid triangles indicate sedimentation of the [$^3$H]RE$_2$ incubated with antibodies bound to the oligopeptide. Open squares designate sedimentation of [$^3$H]RE$_2$ incubated with antibodies preincubated with ER bound to unlabelled E$_2$; solid diamonds designate sedimentation of [$^3$H]RE$_2$ incubated with antibodies preincubated with buffer only.

As shown in FIG. 11, [$^3$H]RE$_2$ alone sediments as a 4.6S complex on SDG/0.4 M KCl while in the presence of MAbs the [$^3$H]RE$_2$ complexes sediment with a S value between 7–8S. When the MAbs were preincubated with the oligopeptide they did not cause any increase in the sedimentation coefficient of [$^3$H]RE$_2$ suggesting that the oligopeptide has occupied the antibody binding site. Clearly, these results indicate that these MAbs are site specific with respect to the domain spanning amino acids 247–261 of the ER.

EXPERIMENTAL SERIES 5: INTERACTIONS OF DNA-BINDING DOMAIN SPECIFIC ANTI-ER MONOCLONAL ANTIBODIES

Figure 12A:
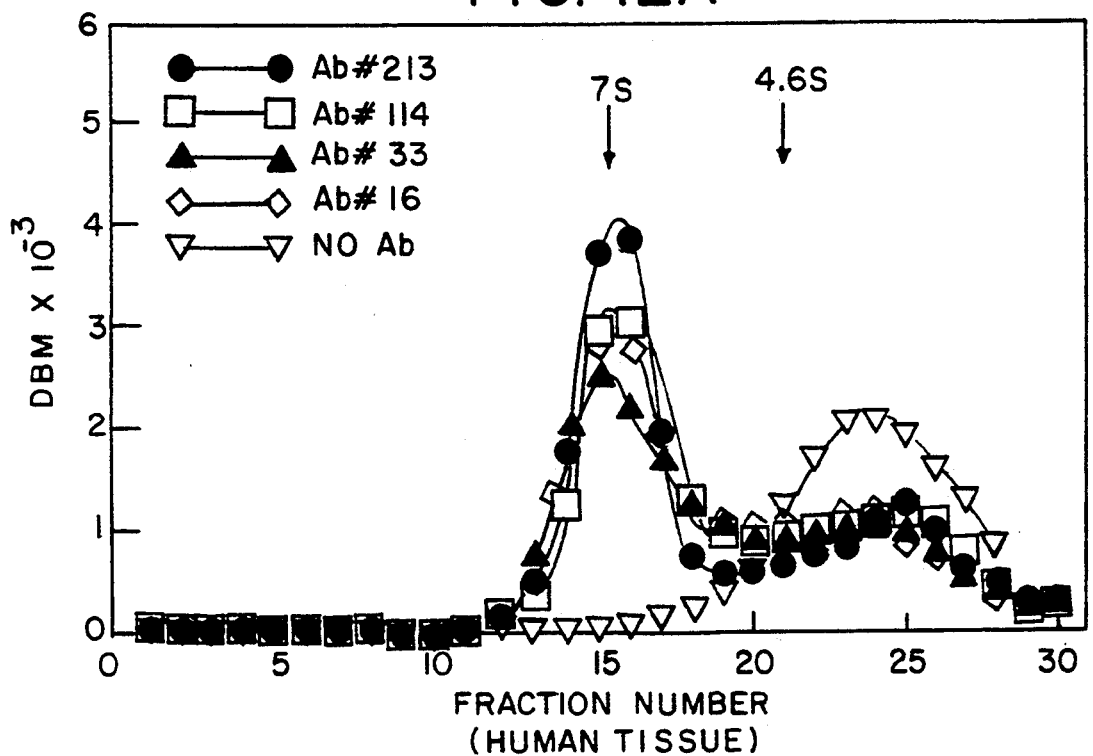
Figure 12B:
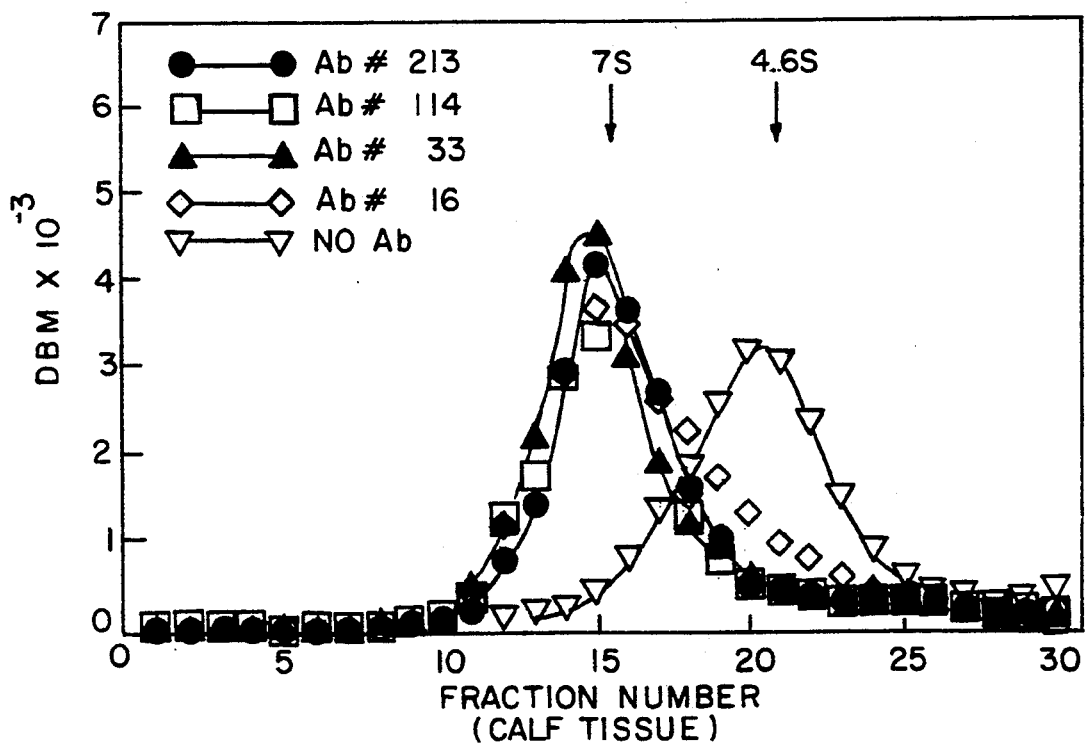
Figure 13A:
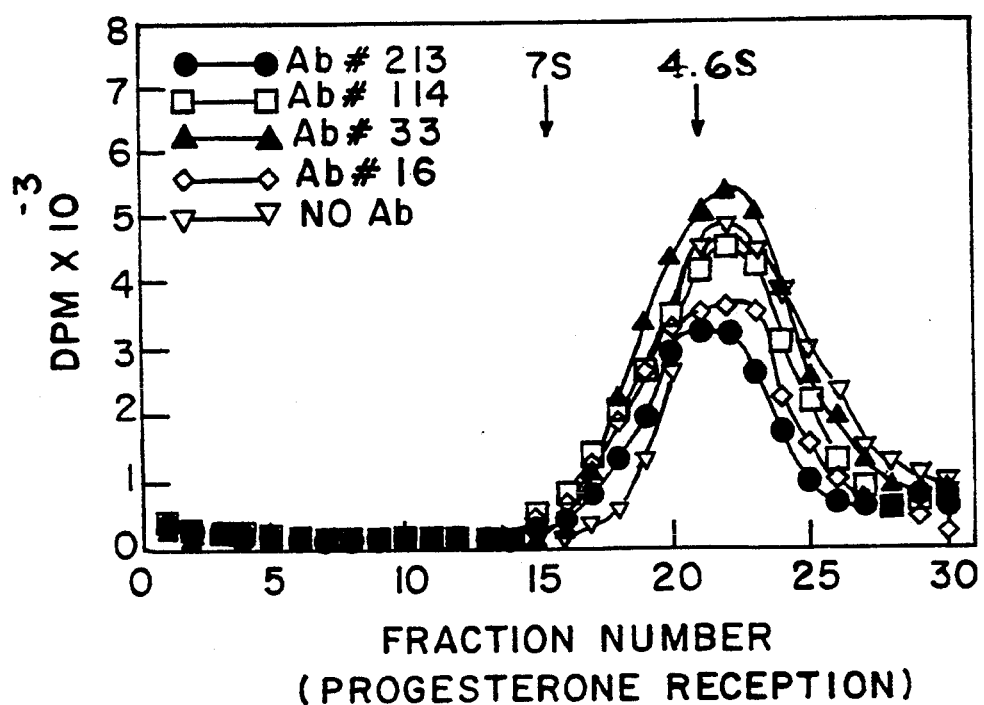
Figure 13B:
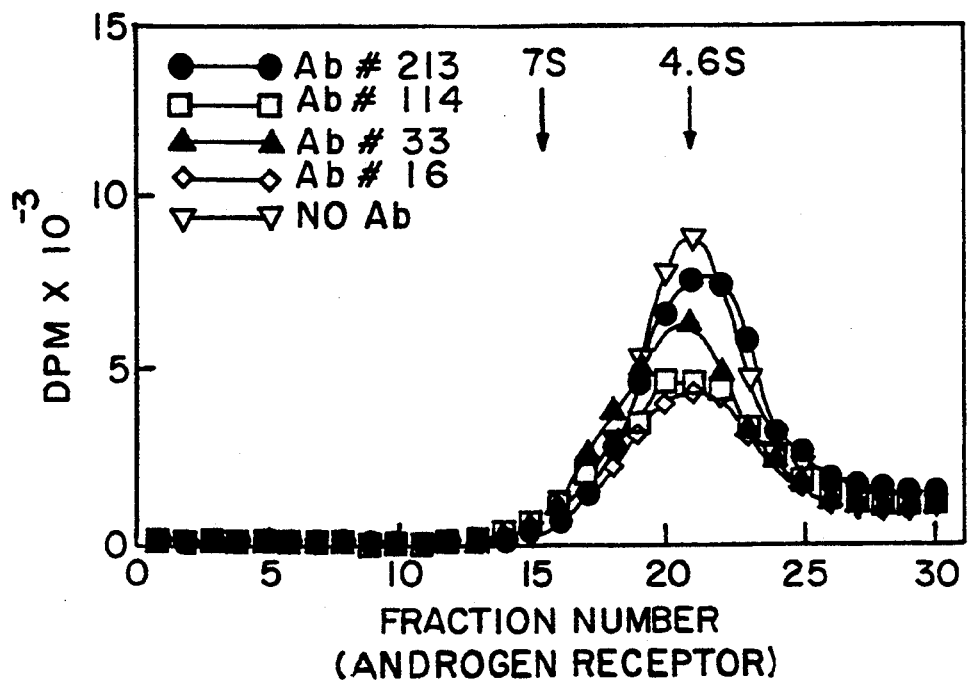
Figure 13C:
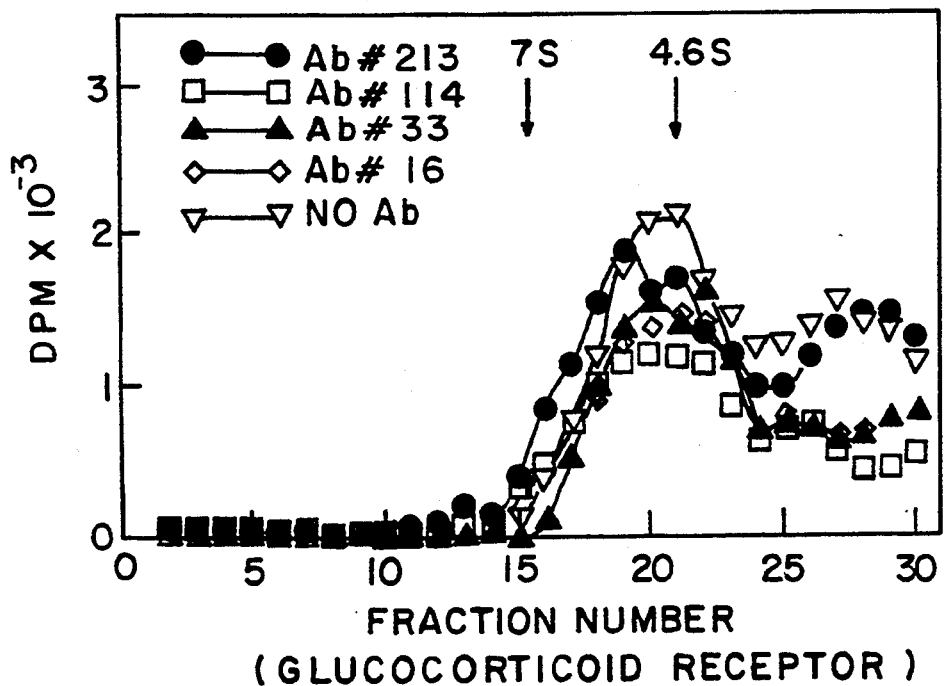
Figure 13D:
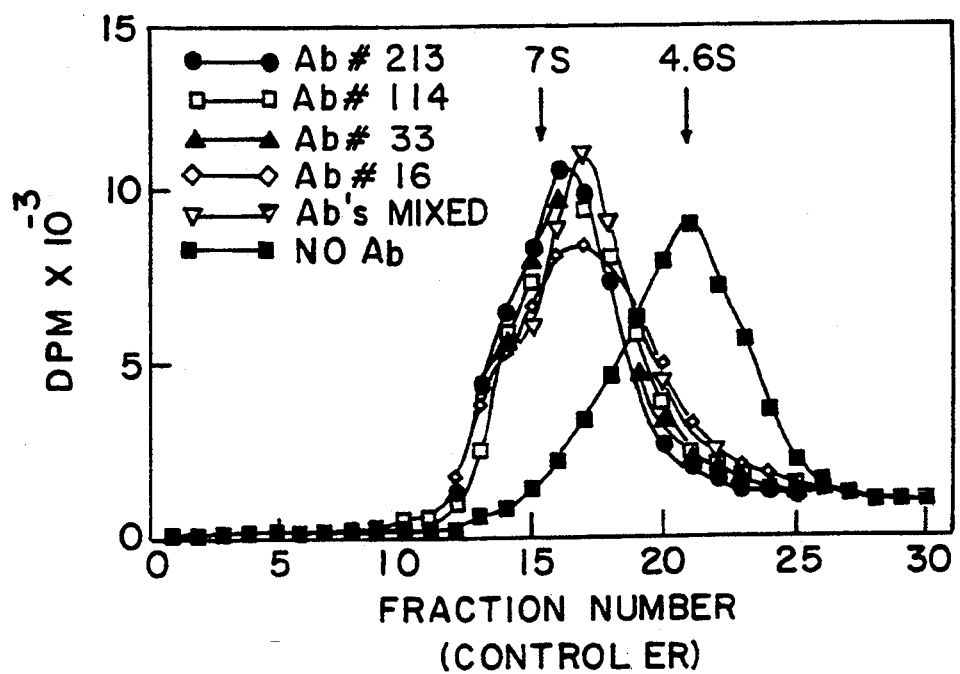

Interaction Of Monoclonal Antibodies Prepared Against Oligopeptide From hER With [$^3$H]RE$_2$ From Various Mammalian Species Several studies have suggested that ER protein has two conserved regions, namely the DNA-binding domain (region "C") and the general steroid binding domain (region "E"). Thus, it is deemed likely that the MAbs produced against the DNA binding domain of hER will interact with ER from various species. To empirically demonstrate this interaction, cytosols from human breast cancer tissue, calf, rat, mouse, and dog uteri were labelled with [$^3$H]E$_2$ for 16 h at 0° C. After removal of free radioactivity with DCC, samples were incubated without (control) or with ascites from clones No. 213, 114, 33, and 16. After 16 h at 0° C. the samples were analyzed by sucrose density gradients as described earlier. The results are given by FIG. 12 in which FIG. 12A represents human breast cancer tissue data; FIG. 12B calf uterine tissue data; FIG. 12C designates rat uterine tissue data; FIG. 12D indicates mouse uterine tissue data; and FIG. 12E illustrates dog uterine tissue data.

A close inspection of FIG. 12 shows that when the [$^3$H]RE$_2$ complexes from various species were incubated with MAbs and analyzed by SDG/0.4 M KCl, an increase in the S values was observed, revealing that [$^3$H]RE$_2$ from these species do in fact cross-react with these MAbs. Note also that each MAb is remarkably consistent in the degree of cross-reaction among the species evaluated.

Receptor Specificity Of Monoclonal Antibodies Prepared Against An Oligopeptide From hER It has been suggested that the DNA binding domain of receptor proteins in the steroid hormone family share 42–95% homology with each other [Evans, R.M., *Science* 240:889 (1988)]. The production of MAbs to this C-binding region of human ER thus was expected to result in MAbs which cross-react with progesterone receptor, glucocorticoid receptor, and androgen receptor The experiment was conducted to test this possibility.

Initially, progesterone receptors of calf uterine cytosol were labelled with [$^3$H]ORG2058; glucocorticoid receptors were labelled by incubating calf uterine cytosol with [$^3$H]dexamethasone; and androgen receptors of rat ventral prostate cytosol were labelled with [$^3$H]DMNT as follows.

Cytosol fractions from each tissue were prepared in the appropriate buffer, as described previously. Briefly, fresh tissue or frozen tissue powder was homogenized (1 g/4 ml) in buffer TT, pH 7.4 at 2° C. The homogenate was then centrifuged at 105,000×g for 45 min at 2° C. and the supernatant fraction (cytosol) was used for receptor binding studies.

To label the ER aliquots of the calf or human breast tissue, cytosols were incubated at 2° C. for 4 h with 5 nM [$^3$H]E$_2$ in the absence (total binding) or presence (non-specific binding) of a 100 fold molar excess of unlabelled DES as previously reported [Muller et al., *J. Biol. Chem.* 258:9227–9236 (1983); Muller et al., *Cancer Res.* 40:2941 (1980)]. Progesterone receptors were labelled by incubating calf uterine cytosol with 15 nM [$^3$H]ORG2058 in the absence or presence of unlabelled ORG2058 as described previously [Traish et al., *Steroids* 47:157 (1986)]. Androgen receptors were labelled by incubating rat prostate cytosol with 10 nM [$^3$H]DMNT in the absence or presence of unlabelled DHT; and glucocorticoid receptors were labelled by incubating calf uterine cytosol with 10 nM [$^3$H] dexamethason in the absence or presence of unlabelled DEX as conventionally known [Traish et al., *Endocrinology* 118:1327 (1986)]. At the end of the incubation free radioactivity was removed with dextran coated charcoal pellets and the supernatant used for antibody-receptor interactions.

Individual aliquots of these labelled receptor preparations were then incubated at 0° C. for 16 h with an aliquot of each of the ascites from the various clones. As a control, other aliquoted samples were incubated with buffer only. All samples were then analyzed on SDG as described previously. The results are shown by FIG. 13A–13D in which panel A represents progesterone receptor; panel B indicates androgen receptor; panel C designates glucocorticoid receptor; and panel D identifies control estrogen receptor.

As graphically illustrated by FIG. 13, when MAbs were incubated with progesterone receptors of calf uterus labelled with [$^3$H]ORG2058, no demonstrable increase in the sedimentation coefficient was observed revealing that these MAbs do not cross-react with the native form of the progesterone receptor. Similarly, when rat prostatic androgen receptors labelled with [$^3$H]DMNT or glucocorticoid receptors from calf uterine tissue labelled with [$^3$H]DEX were incubated with MAbs and analyzed on SDG/0.4 M KCl, no increase in the sedimentation coefficient of these receptor proteins was observed. Under identical conditions, however, these MAbs increased the S value of the [$^3$H]RE$_2$ complexes particularly in comparison to the data provided by FIG. 10. The data of FIG. 13 clearly show that these MAbs are specific for the native form of ER and do not bind to the native form of other steroid receptors.

Interaction Of Mab No. 213 With Increasing Concentrations Of [$^3$H]RE$_2$ Followed By SDG Analysis The interactions of these MAbs with [$^3$H]RE$_2$ were examined under conditions in which the concentrations of the MAbs were kept constant while increasing the concentration of [$^3$H]RE$_2$. Calf uterine cytosol was prepared and labelled as described previously. Samples of this cytosol with different [$^3$H]RE$_2$ concentrations were then removed and incubated with Mab No. 213 for 16 h at 0° C. Individual samples were then analyzed on SDG as graphically illustrated in FIG. 14.

As demonstrated by the data of FIG. 14, at all concentrations of ER tested (20 fmol–1,000 fmol), MAb No.

213 (at 100 ug as in FIG. 14A and at 25 ug as in FIG. 14B) and Mab No. 16 (at 25 ug as in FIG. 14C) caused an increase in the S value of [$^3$H]RE$_2$. Similar profiles were obtained with MAbs No. 16, 33, and 114 (data not shown).

Interaction Of Monoclonal Antibody No. 213 With The Unoccupied ER

The ability of MAb No. 213 to bind to the unoccupied ER was also evaluated. The latter was incubated with the MAb and analyzed on SDG containing 0.4 M KCl. Specifically, calf uterine cytosol was incubated in the presence of MAb No. 213 for 16 h at 0° C. Another aliquot of the cytosol was first labelled with [$^3$H]E$_2$ and then incubated in the absence or presence of MAb No. 213. Samples were layered on sucrose density gradients as described previously. After fractionation, the fractions from the unoccupied ER sample were reincubated at 0° C. for 16 h with [$^3$H]E$_2$ in the absence or presence of 5 uM DES. The bound radioactivity was then determined with dextran coated charcoal. The results are graphically illustrated by FIG. 15.

As shown in FIG. 15, MAb No. 213 bound to the unoccupied ER. The loss of ER as observed was most likely due to the instability of the ER in the unoccupied state, since incubation with antibody and the subsequent analysis on SDG was performed with the unoccupied receptor form.

Equilibrium Binding Of [$^3$H]RE$_2$ To Monoclonal Antibodies Coupled To Sepharose To determine the apparent equilibrium association and dissociation constants, each MAb was first conjugated with sepharose and then incubated with [$^3$H]RE$_2$ in the absence (total binding) or presence of increasing concentrations of DES-bound ER. This was performed as follows.

Calf uterine cytosol was prepared and divided into two aliquots. One sample was incubated with 10 nM of unlabelled E$_2$ at 0° C. for 16 h. The other sample was divided and incubated with [$^3$H]E$_2$ in absence or presence of 5 uM DES. The sample containing the estrogen receptor bound to unlabelled E$_2$ was treated with DCC and aliquots (final volume of 1 ml) containing 0-4,000 femtomoles of RE$_2$ were incubated with monoclonal antibodies conjugated to sepharose in buffer containing 0.4 M KCl at 0°-4° C. for 16 h with continuous agitation. At this point, cytosol labelled with [$^3$H]RE$_2$ was treated with DCC and a fixed concentration (300 femtomoles) of [$^3$H]RE$_2$ was then added to each MAb-sepharose incubation and allowed to bind for an additional 16 h at 0° C. The bound [$^3$H]RE$_2$ was determined by centrifugation and washing the sepharose-antibody conjugated three times with PBS and subsequent extraction of radioactivity with ethanol. Non-specific binding was determined by incubation with nonrelated monoclonal antibody conjugated to sepharose. The binding data was corrected for non-specific binding and analyzed according to the method of Mukku [J. Biol. Chem. 259:6543 (1984)]. The results are graphically illustrated by FIGS. 16A-16D in which FIG. 16A identifies MAb No. 213; FIG. 16B represents MAb No. 114; FIG. 16C indicates MAb No. 33; and FIG. 16D designates MAb No. 16.

As shown in FIG. 16, increasing concentrations of ER bound to unlabelled DES competed effectively for [$^3$H]RE$_2$ binding. These data were then analyzed according to the isotope dilution method after subtraction of non-specific binding. The estimated equilibrium dissociation constants as calculated from scatchard plots, ranged from 0.4 nM to 1.8 nM demonstrating that the MAbs have high affinity for the receptor. Similarly, since SDG requires 16-20 h of centrifugation under non-equilibrium conditions, the stability of the [$^3$H]RE$_2$ MAb complexes also reveals that these MAbs are of high affinity.

Overall Summary of MAb Properties

The MAbs obtained against the No. 3 oligopeptide bind to ER from various species including human, calf, rat, dog, and mouse tissues, suggesting that this particular domain of ER is highly conserved in many species. The DNA-binding domain of hER (amino acids 185-263) has some homology with steroid and other nuclear receptors. Since the homology among these proteins varies from 42% to 95%, and this region appears to be conserved, one would expect that MAbs obtained against a specific oligopeptide sequence from this region would cross-react with some of these receptors. The data clearly show that no cross-reactivity existed when these MAbs were incubated with the native form of progesterone receptor, glucocorticoid receptor, or androgen receptor.

In addition, seven monoclonal antibodies (No. 16, 33, 35, 36, 114, 213, and 318) recognized the native ER by immunoprecipitation assay. Only four of these (16, 33, 114, and 214) remained tightly bound to ER in SDG containing 0.4 M KCl. This interaction reflects high affinity since the complex (ER/Ab) remained undissociated for 18 h under non-equilibrium conditions. The antibodies share the same epitope since an equal mixture of these antibodies did not significantly increase the S value of the antibody-ER complex when compared to the simple antibody-receptor complex. This shows that the binding site represented by the 15 amino acid oligopeptide is preserved in the native ER molecule. Specificity was further confirmed by experiments in which the peptide was used as a competitor. All four antibodies were unable to bind to ER when incubated with the free oligopeptide prior to addition of labelled ER. Under the conditions employed here, the antibodies at a fixed concentration recognized ER concentrations between 20 and 1,000 femtomoles. This is consistent with the high affinity for ER. The binding of the antibodies to ER is also independent of the ligand binding under the conditions employed.

V. Ability Of The DNA-Binding Domain Specific Antibodies To Inhibit Binding Of Activated Estrogen Receptors To DNA This series of experiments share a variety of different methods and materials as part of their individual protocols. These include the following.

Formation Of Salt Activated (4S) And Heat Transformed (5S) Estrogen Receptor Complexes The salt induced activation and the heat transformation of estrogen receptors was carried out as described in the literature [Muller et al., J. Biol. Chem. 258:9227-9236 (1983)]. Briefly, cytosol labelled with 5 nM [$^3$H]E$_2$ for 1-3 h at 0° C. was divided into three samples and treated as follows: one sample was incubated at 28° C. for 45 min to induce heat transformation. All samples were then treated with dextran coated charcoal to remove free [$^3$H]E$_2$. One heated (5S) and one unheated sample received 0.1 volume of 4M KCl solution to yield 0.4 M KCl in the final incubation.

This treatment does not influence the heat transformed receptor but induces salt activation of the untreated receptor. The control (unheated) sample received 0.1 volume of buffer and was kept at 0° C. This represents the unactivated untransformed estrogen receptor.

DNA-Cellulose Binding Assay

The ability of activated and transformed estrogen receptors to bind to DNA-cellulose was determined as conventionally described [Muller et al., *J. Biol. Chem.* 258:9227–9236 (1983); Bailey et al., *J. Biol. Chem.* 255:2729–2734 (1980)]. Briefly, DNA-cellulose (Sigma) was washed with 1 M KCl in buffer TGT/MO and then resuspended in TGT/MO buffer and washed four times to remove KCl. The hydrated resin was resuspended in TGT/MO and 0.5 ml aliquots (100 ug DNA) were dispensed into siliconized test tubes. Aliquots of the labelled cytosols were then added and the mixture kept in suspension by frequent mixing on a vortex mixer. After 1 h at 0° C. the bound estrogen receptor-DNA complexes were separated by centrifugation at 2° C. for 10 min at 2,000×g. The pellets were washed three times by resuspension in 5 ml buffer and centrifugation. The final pellet was extracted with 2 ml of absolute ethanol and the radioactivity counted. Binding to DNA was expressed as percent of total specifically bound $[^3H]RE_2$ added to DNA-cellulose.

Labelling Of Nuclear Estrogen Receptors With $[^3H]E_2$ In-Situ

Uteri of immature 22 day old female rats were incubated (5 uteri/ml) in medium M199 at 37° C. for 1 h with 5 nM $[^3H]E_2$ in the absence (total binding) or presence (non-specific binding) of 5 uM DES as described in the literature [Muller et al., *J. Biol. Chem.* 255:4062–4067 (1980)]. The uteri were then rinsed in ice cold TGT/MO buffer and then homogenized (5 uteri/ml) in TGT/MO buffer containing 1.5 mM EDTA. The homogenate was centrifuged at 1,000×g at 2° C. for 10 min to obtain the crude nuclear fraction. This fraction was then washed three times with TGT/MO buffer by resuspension and centrifugation. The final pellet was extracted with TGT/MO containing 0.4 M KCl for 1 h at 0° C. The sample was then centrifuged at 100,000×g for 30 min and the supernatant containing the solubilized 5S estrogen receptor was removed and used for analysis of antibody-receptor interaction on sucrose density gradients.

EXPERIMENTAL SERIES 6: DNA BINDING STUDIES

Inhibition Of Binding Of Salt-Activated (4S) And Heat Transformed (5S) Estrogen Receptors To DNA-Cellulose Calf uterine cytosol was prepared in TGT buffer and labelled with $[^3H]E_2$ as described above. Aliquots of this labelled cytosol were then dispensed into separate test tubes and either kept at 0° C. without any addition (sample A), treated with 0.1 volume of 4 M KCl (samples B-F) for 1 h at 0° C., or heated at 28° C. for 45 minutes (samples G-I). Samples were then incubated in the presence of buffer only (A and B), preimmune serum (C), antiserum AT2A (D and G), antiserum AT3A (E and H), or antiserum AT3B (F and I). After 16 h of incubation at 0° C. all samples were diluted with buffer. This reduced the KCl concentrations to 0.1 M so it would not interfere with subsequent analysis on DNA-cellulose. Aliquots were then added to DNA-cellulose suspension to measure receptor activation and additional aliquots were removed for assay of total bound radioactivity. The DNA-cellulose/cytosol mixture was kept at 0° C. for 1 h with frequent mixing on a vortex mixer and the fraction of the receptors bound to DNA-cellulose was determined as previously described.

The results are graphically provided by FIG. 17. All data points were corrected for non-specific binding and represent the average of two separate experiments. The shaded bars represent the heat transformed 5S ER. The open bars represent the unactivated or KCl-activated 4S estrogen receptors.

As shown in FIG. 17, unactivated and untransformed $[^3H]RE_2$ complexes, labelled and maintained at 0° C., do not bind appreciably (3%) to DNA-cellulose (sample A). Activation of $[^3H]RE_2$ by KCl and subsequent dilution of the KCl to 0.1 M increased binding of $[^3H]RE_2$ to DNA to 40% (sample B). Incubation of salt activated $[^3H]RE_2$ complexes with either preimmune serum or with AT2A did not inhibit DNA binding (43%, 40%) of $[^3H]RE_2$ to DNA (samples C and D). Incubation of salt activated $[^3H]RE_2$ with antisera AT3A and AT3B, however, resulted in inhibition of $[^3H]RE_2$ binding to DNA (samples E and F). This reveals that antisera AT3A and AT3B interacted with the DNA binding region of the ER. Incubation of the antisera with the heat transformed $[^3H]RE_2$ complexes showed inhibition of DNA binding similar to that observed with KCl activated $[^3H]RE_2$. Both antisera AT3A and AT3B inhibited DNA binding (samples H and I). Antiserum AT2A did not inhibit significantly the binding of DNA (sample G).

Analysis Of Antisera Binding To ER Complexes Activated By KCl

To demonstrate that the antibodies remained bound to $[^3H]RE_2$ complexes during prolonged incubation, aliquots of the $[^3H]RE_2$ which were exposed to KCl and the antibodies for 16 h at 0° C. were then analyzed by sucrose density gradient analysis in the presence of KCl.

Specifically, labelled $[^3H]RE_2$ complexes prepared as described for FIG. 17 were incubated with or without KCl for 1 h at 0° C. Subsequently, samples were incubated with the antisera as described above. Aliquots of each sample were then diluted with buffer and analyzed on sucrose density gradients containing 0.4 M KCl. The results are given by FIG. 18 in which the unactivated ER in absence of antiserum are represented by open circles; KCl-activated ER in absence of antiserum are identified by solid circles; KCl-activated ER incubated with preimmune serum are indicated by open triangles; KCl-activated ER incubated with AT2A antiserum are designated by solid triangles; KCl-activated ER incubated with antiserum AT3A are illustrated by open squares; and KCl-activated ER incubated with antiserum AT3B are delineated by solid squares.

As shown in FIG. 18, antisera AT3A and AT3B caused an increase in the sedimentation coefficient of the KCl activated $[^3H]ER$. Antiserum AT2A caused an increase only in about one-third of the complexes. $[^3H]RE_2$ exposed to KCl and incubated with preimmune sera, or buffer, only sedimented as 5.6S complexes with a shoulder in the 4.6S region. This is probably due to partial dimerization of the receptor protein upon dilution prior to SDG analysis. The non-activated

[³H]ER sedimented at 4.6S with a shoulder in the 5S region.

Dose-Dependent Inhibition Of KCl-Activated ER Binding To DNA By Anti-Estrogen Receptor Antisera Calf uterine cytosol was prepared in buffer TGT and labelled with [³H]E$_2$. The resulting [³H]RE$_2$ complexes were then activated by incubation with KCl (0.4 M) for 1 h at 0° C. Individual aliquots were then incubated without (control) or with various volumes of the antisera. After incubation for 16 h 0° C. samples were assayed for the ability of [³H]RE$_2$ to bind to DNA as described previously. All recorded data were corrected for non-specific binding and each point represents the average of three determinations. The results are given by FIG. 19 in which antiserum AT2A is represented by solid circles; antiserum AT3A is identified by solid triangles, and antiserum AT3B is designated solid squares.

As shown in FIG. 19, antisera AT3A and AT3B inhibited DNA binding in a dose-dependent manner. Fifty percent inhibition was observed with 10 ul of antisera. Antiserum AT2A did not inhibit DNA binding even at 150 ul, a concentration which causes more than 70% of [³H]RE$_2$ complexes to sediment at a greater rate than the control.

Binding Of DNA To KCl-Activated [³H]RE$_2$ Complexes Prevents Subsequent Interactions Of The Antisera With The Estrogen Receptors

[³H]RE$_2$ complexes were prepared, labelled, and KCl-activated as described earlier. Aliquots were then incubated with DNA-cellulose at 0° C. for 1 h to promote [³H]RE$_2$ binding to DNA. The DNA-cellulose was then washed three times with buffer to remove unbound [³H]RE$_2$ complexes and then reincubated for 2 h at 0° C. with preimmune sera (sample A), antiserum AT2A (sample B), antiserum AT3A (sample C), and antiserum AT3B (sample D). At the end of the incubation the DNA-cellulose samples were washed and the radioactivity was extracted and counted. The results are given by FIG. 20. All data represent specific binding and each data point represents the average of three determinations.

As shown in FIG. 20, preimmune sera did not affect the [³H]RE$_2$ complexes bound to DNA (sample A). Similarly, antiserum AT2A did not influence the [³H]RE$_2$ complexes bound to DNA (sample B). Antiserum AT3A reduced the binding of [³H]RE$_2$ from 57 to 35%, suggesting that only the [³H]RE$_2$ dissociated from DNA during the incubation was bound to the antibody (sample C). Antiserum AT3B slightly reduced from 57 to 42%) the bound [³H]RE$_2$ complexes. This demonstrates that once bound to DNA the [³H]RE$_2$ complexes do not bind to the antibody. Rather, only when these complexes dissociate from the DNA do they become accessible to the antibody.

Overall Summary

Characterization of these antibodies with respect to receptor specificity, species specificity, and titer has shown that these antisera were site specific since the oligopeptides, when present in excess, displaced ER binding to the antibodies. It was previously demonstrated that these antisera recognized the 8S, 4S, and 5S cytosolic ER forms. These experiments show that the antisera also bind to the nuclear KCl-extractable 5S ER complexes labelled with [³H]RE$_2$ in-vitro. The incomplete binding of the 5S extractable nuclear ER by the antisera was probably due to the low affinity exhibited by all of the antisera towards the rat uterine estrogen receptor.

Although several reports have suggested that the region with amino acids 185–263 is the putative DNA-binding region, antiserum AT2A which was developed against the oligopeptide with amino acids 231–245, did not inhibit DNA-binding of salt activated and heat transformed ER. In contrast, antisera AT3A and AT3B which were raised against an oligopeptide with sequences spanning amino acids 247–261, inhibited completely the binding of salt activated and heat transformed ER. The inhibition of DNA binding by the antisera AT3A and AT3B was specific since neither the preimmune serum nor the antiserum AT2A were able to inhibit the DNA binding of salt activated and heat transformed ER.

The present invention is not to be restricted in form nor limited in scope except by the claims appended hereto.

What we claim is:

1. A monoclonal antibody specific for an epitope within amino acid residues 247–261 of human estrogen receptor protein, said monoclonal antibody having binding specificity for a single epitope within the DNA-binding domain in the activated but untransformed (4S) forms and in the activated and transformed (5S) forms of human estrogen receptor protein but which does not bind with the native (8S) forms of human estrogen receptor protein.

2. A hybridoma which produces a monoclonal antibody specific for an epitope within amino acid residues 247–261 of human estrogen receptor protein, said hybridoma comprising an antibody producing cell producing a monoclonal antibody having binding specificity for a single epitope within the DNA-binding domain in the activated but untransformed (4S) forms and in the activated and transformed (5S) forms of human estrogen receptor protein but which does not bind with the native (8S) forms of human estrogen receptor protein; and a tumor cell fused with said antibody producing cell.

* * * * *